United States Patent [19]

Rubin

[11] Patent Number: 5,374,287
[45] Date of Patent: Dec. 20, 1994

[54] DEFIBRILLATOR AND DEMAND PACER CATHETERS AND METHODS FOR USING SAME

[75] Inventor: Leo Rubin, Suffern, N.Y.

[73] Assignee: British Technology Group USA Inc., Gulph Mills, Pa.

[21] Appl. No.: 37,628

[22] Filed: Mar. 24, 1993

Related U.S. Application Data

[63] Continuation-in-part of Ser. No. 683,450, Apr. 10, 1991, abandoned.

[51] Int. Cl.$^5$ .............................................. A61N 1/39
[52] U.S. Cl. ................................. 607/131; 607/5; 607/122
[58] Field of Search ................ 607/2, 4, 5, 122, 123, 607/130, 131; 128/898

[56] References Cited

U.S. PATENT DOCUMENTS

| | | | |
|---|---|---|---|
| Re. 27,652 | 5/1973 | Mirowski et al. | 128/419 D |
| 3,857,398 | 12/1974 | Rubin | 128/419 P |
| 3,915,174 | 10/1975 | Preston | 128/419 P |
| 3,942,536 | 3/1976 | Mirowski et al. | 128/419 D |
| 4,106,512 | 8/1978 | Bisping | 128/418 |
| 4,161,952 | 7/1979 | Kinney et al. | 128/786 |
| 4,332,259 | 6/1982 | McCorkle, Jr. | 128/786 |
| 4,481,953 | 11/1984 | Gold et al. | 128/786 |
| 4,550,737 | 11/1985 | Osypka | 128/785 |
| 4,633,880 | 1/1987 | Osypka | 128/642 |
| 4,641,656 | 2/1987 | Smits | 128/419 D |
| 4,646,755 | 3/1987 | Kane | 128/785 |
| 4,708,145 | 11/1987 | Tacker, Jr. et al. | 128/419 D |
| 4,727,877 | 3/1988 | Kallok | 128/419 D |
| 4,817,608 | 4/1989 | Shapland et al. | 607/4 |
| 4,922,927 | 5/1990 | Fine et al. | 128/419 P |
| 5,003,990 | 4/1991 | Osypka | 128/772 |
| 5,014,696 | 5/1991 | Mebra | 128/419 D |
| 5,044,375 | 9/1991 | Bach, Jr. et al. | 128/786 |
| 5,050,601 | 9/1991 | Kupersmith et al. | 607/2 |
| 5,143,090 | 9/1992 | Dutcher et al. | 607/131 |

FOREIGN PATENT DOCUMENTS

| | | | |
|---|---|---|---|
| 219608 | 4/1987 | European Pat. Off. | A61N 1/05 |
| 489965 | 6/1992 | European Pat. Off. | A61N 1/05 |
| 491082 | 6/1992 | European Pat. Off. | A61N 1/05 |
| 4108269 | 6/1992 | Germany | A61B 5/0464 |

OTHER PUBLICATIONS

G. Hossein Almassi, M.D., et al. "Constrictive Pericarditis Associated with Patch Electrodes of the Automatic Implantable Cardioverter-Defibrillator," *Chest*, Aug. 1987, at 369–371.

Gust H. Bardy, M.D., et al. "Evaluation of Electrode Polarity on Defibrillation Efficacy," *American Journal of Cardiology*, Feb. 15, 1989, at 433–437.

Gust H. Bardy, et al. "A Prospective, Randomized Evaluation of Biphasic vs. Monophasic Pulses on Epicardial Defibrillation Efficacy in Man," *Abstracts of the 61st Scientific Sessions*, Supplement II Circulation, vol. 78, No. 4, Oct. 1988, at 219.

Gust H. Bardy, et al. "Transvenous Coronary Sinus to Right Ventricular Catheter Defibrillation in Man,"

(List continued on next page.)

*Primary Examiner*—George Manuel
*Attorney, Agent, or Firm*—Workman, Nydegger & Jensen

[57] ABSTRACT

A defibrillator and demand pacer catheter is defined by a flexible, electrically nonconductive probe having an electrically conductive pathway longitudinally disposed therein. Attached to one end of the probe is a defibrillator electrode capable of anchoring the probe to the septum of a heart and of transmitting from said conductive pathway directly to the interior of the septum a portion of an electrical defibrillation pulse sufficient to defibrillate the heart. The defibrillation pulse is delivered in such a manner so as to avoid injuring the heart tissue immediately adjacent to the defibrillator electrode. In the preferred embodiment, the defibrillator electrode is helical; however, it is also envisioned as being a lance. Alternatively, the catheter further comprises a ground electrode, a demand pacer electrode, and a supplemental defibrillator electrode attached to the probe.

16 Claims, 15 Drawing Sheets

OTHER PUBLICATIONS

*Abstracts of the 61st Scientific Sessions,* Supplement II Circulation, vol. 78, No. 4, Oct. 1988, at 220.

Joseph Borbola, M.D., et al. "The Automatic Implantable Cardioverter–Defibrillator," *Arch Intern Med,* vol 148, Jan. 1988, at 70–76.

Annette M. Brodsky, et al. "Psychosocial Adaptation to the Automatic Implantable Cardioverter Defibrillator," *Abstracts of the 61st Scientific Sessions,* Supplement II Circulation, vol. 78, No. 4, Oct. 1988, at 155.

P. Brugada, et al. "Electrophysiology, Heart Rate and Rhythm," *Circulation* 1989, at 113–114.

Hugh Calkins, M.D., et al. "Pacemaker/Implantable Defibrillator Interactions: Are They of Clinical Importance?, etc. . . . " Abstract, *Journal of the American College of Cardiology,* vol. 13, No. 2, Feb. 1989, at 66A.

Reto A. Candinas, M.D., et al. "Sudden Cardiac Death," *Contemporary Internal Medicine,* Jan. 1991, at 15–20, 23–25.

Peter D. Chapman, M.D., et al. "Comparison of Monophasic, Biphasic, and Triphasic Truncated Pulses for Non–Thoracotomy Internal Defibrillation," Abstract, *Journal of the American College of Cardiology,* vol. 11, No. 2, Feb. 1988, at 57A.

Michael G. Deeb, M.D., et al. "Lead Systems for Internal Ventricular Fibrillation," *Circulation,* vol 64, No. 2, Aug. 1981, at 242–245.

Eric S. Fain, Sc.B., et al. "Internal Cardiac Defibrillation: Histopathology and Temporal Stability of Defibrillation Energy Requirements," *Journal of the American College of Cardiology,* vol. 9, No. 3, Mar. 1987, at 631–638.

John Fontaine, et al. "'Concealed' Entrainment of Ventricular Tachycardia A Manifestation of Auto Decremental Overdrive Pacing," *Abstracts of the 61st Scientific Sessions,* Supplement II Circulation, vol. 78, No. 4, Oct. 1988, at 237.

Osamu Fujimura, et al. "Effects of Time to Defibrillation on Defibrillation Success and Post Defibrillation Arrhythmias," *Abstracts of the 61st Scientific Sessions,* Supplement II Circulation, vol. 78, No. 4, Oct. 1988, at 219.

Leonard A. Golding, et al. "Late Results of Implanted Defibrillators," *Abstracts of the 61st Scientific Sessions,* Supplement II Circulation, vol. 78, No. 4, Oct. 1988, at 440.

Thomas Guarnieri, M.D., et al. "Success of Chronic Defibrillation and the Role of Antiarrhythmic Drugs with the Automatic Implantable Cardioverter–Defibrillator," *The American Journal of Cardiology,* vol. 60, Nov. 1, 1987, at 1061–1064.

Raymond E. Ideker, M.D., Ph.D., et al. "Cardiac Mapping at Duke Medical Center," *American Journal of Cardiology,* vol. 63, at 17F–29F.

Richard W. Illes, et al. "Amelioration of Postischemic Stunning by Deferoxamine-Blood Cardioplegia," *Abstracts of the 61st Scientific Session,* Supplement II Circulation, vol. 78, No. 4, Oct. 1988, at 440.

Douglas L. Jones, PhD., et al. "Sequential Pulse Defibrillation in Humans: Orthogonal Sequential Pulse Defibrillation with Epicardial Electrodes," *Journal of the American College of Cardiology,* vol. 11, No. 3, Mar. 1988, at 590–596.

Michael J. Kallok, Ph.D., et al. "Catheter Electrode Defibrillation in Dogs: Threshold Dependence on Implant Time and Catheter Stability," *American Heart Journal,* vol. 109, No. 4, Apr. 1985, at 821–826.

R. E. Kerber, et al. "Medical Instrumentation," *Journal of the Association for the Advancement of Medical Instrumentation,* Jan.–Feb. 1978, at 55.

Michael H. Lehmann, M.D., F.A.C.C., et al. "Effect of Successful Defibrillation on Subsequent Defibrillation Threshold in a Canine Model of Rapidly Recurring Cardiac Arrest," Abstract, *Journal of the American College of Cardiology,* vol. 13, No. 2, Feb. 1989, at 66A.

Michael H. Lehmann, M.D., et al. "Sudden Cardiac Death (SCD) in Patients with an Automatic Implantable Cardioverter Defibrillator (AICD): Report of 57 Cases," *Abstracts of the 61st Scientific Sessions,* Supplement II Circulation, vol. 78, No. 4, Oct. 1988, at 155.

Bruce B. Lerman, et al. "Current–Based Defibrillation: A Prospective Study," *Abstracts of the 61st Scientific Sessions,* Supplement II Circulation, vol. 78, No. 4, Oct. 1988, at 45.

Bruce B. Lerman, et al. "Adverse Effects of AICD Epicardial Patches on Transthoracic Defibrillation," *Abstracts of the 61st Scientific Sessions,* Supplement II Circulation, vol. 78, No. 4, Oct. 1988, at 155.

Bruce B. Lerman, et al. "Distribution of Thoracic Current During Defibrillation in Man: Relationship to Transmyocardial Current," *Abstracts of the 61st Scien-*

(List continued on next page.)

OTHER PUBLICATIONS tific Sessions, Supplement II Circulation, vol. 78, No. 4, Oct. 1988, at 237.

Federico Lombardi, et al. "Signal Averaging of Pre-extrasystolic Beats in Patients With Ventricular Arrhythmias," *Abstracts of the 61st Scientific Sessions*, Supplement II Circulation, vol. 78, No. 4, Oct. 1988, at 237.

Hugh F. McAlister, M.D., et al. "Automatic Implantable Cardioverter Defibrillator: Analysis of Spontaneous Shocks," Abstract, *Journal of the American College of Cardiology*, vol. 13, No. 2, Feb. 1989, at 66A.

David C. McGregor, M.D., et al. "The Porous-Surfaced Electrode," *Journal of Throacic & Cardiovascular Surgery*, vol. 78, No. 2, Aug. 1979, at 281-291.

Martin M. Masterson, M.D., et al. "Atrial Pacemaker Leads Compared," *Cleveland Clinical Journal of Medicine*, Jul.-Aug. 1990, at 433-436.

Malte Meesman, M.D., et al. "Effects of Current Strength and Unipolar Versus Bipolar Pacing at Sites of Infarction of Myocardial Activation Times," Abstract, *Journal of the American College of Radiology*, vol. 11, No. 2, Feb. 1988, at 58A.

Rahul Mehra, et al. "Reduction of Transvenous Defibrillation Thresholds With An Asymmetric Biphasic Pulse," *Abstracts of the 61st Scientific Sessions*, Supplement II Circulation vol. 78, No. 4, Oct. 1988.

Alfred C. Nocolosi, et al. "Simulated Intraoperative Electrophysiologic Study in Dogs-Effects on Left Ventricular Function," *Abstracts of the 61st Scientific Sessions*, Supplement II Circulation, vol. 78, No. 4, Oct. 1988, at 440.

Akihiko Nogami, et al. "Usefulness of Early versus Late Programmed Ventricular Stimulation Study in Patients with Acute Myocardial Infarction," *Abstracts of the 61st Scientific Sessions*, Supplement II Circulation, vol. 78, No. 4, Oct. 1988, at 45.

Michael Oeff, M.D., et al. "Determinates of Defibrillation Threshold," Abstract, *Journal of the American College of Cardiology*, vol. 11, No. 2, Feb. 1988, at 57A.

Michael J. Reiter, M.D., Ph.D., et al. "Effects of Ventricular Fibrillation and Defibrillation on Pacing Threshold in the Anesthetized Dog," *Journal of the American College of Radiology*, vol. 13, No. 1, Jan. 1989, at 180-184.

Kenneth L. Ripley, et al. "Evaluation of Techniques for Recognition of Ventricular Arrhythmias by Implanted Devices," *IEEE Transactions on Biomedical Engineering*, vol. 36, No. 6, Jun. 1989, at 618-624.

L. Rubin, et al., "Automatic Defibrillation and Pacing with a Transvenous Electrode," *Proceedings of the Fourth New England Bioengineering Conference*, May 7-8, 1976, at 427-430.

Leo Rubin, M.D., Ph.D., et al. "Effect of Defibrillation Energy on Pacing Threshold," *Medical Instrumentation*, vol. 17, No. 1, Jan.-Feb. 1983, at 15-17.

Leo Rubin, M.D., et al. "Epicardial Versus Parietal Pericardial Defibrillation," *Presented at the 5th Purdue Conference on CPR & Defibrillation W. Lafayette, Ind.*, Sep. 25-26, 1984.

Leo Rubin, M.D., et al. "Preliminary Data on New Small Titanium Mesh Disc Electrode for Epicardial Defibrillation," *Presentation at NASPE 10th Annual Scientific Session*, May 4-6, 1989.

Leo Rubin et al. "Comparison of Titanium-Mesh and Porous Disc Electrodes for Epicardial Defibrillation," *PACE*, vol. 14, Nov. 1991, Part II, at 1860-1864.

Yusaku Sakakibara, M.D., et al. "Electrophysiologic Effects of Different K+ Concentrations on the Rabbit Atrioventricular Node," Abstract, *Journal of the American College of Radiology*, vol. 11, No. 2, Feb. 1988, at 58A.

Sanjeev Saksena, M.D., et al. "Initial Clinical Experience with Endocardial Defibrillation Using an Implantable Cardioverter/Defibrillator with a Triple-Electrode System," *Arch Intern Med*, vol 149, Oct. 1989, at 2333-2339.

Sanjeev Saksena, M.D. "Endocardial Lead Systems for Implantable Cardioverter Defibrillators: Uncertain Progress Beyond Base Camp," *PACE*, vol. 15, Feb. 1992, at 123-125.

Sanjeev Saksena, M.D., et al. "Long-Term Multicenter Experiment With a Second-Generation Implantable Pacemaker-Defibrillator in Patients With Malignant Ventricular Tachyarrhythmias," *Journal of the American College of Cardiology*, vol. 19, No. 3, Mar. 1, 1992, at 490-499.

S. Saksena, et al. "Initial Clinical Experience with an Implantable Cardioverter-Defibrillator Using a Nonepicardial Electrode System," *Abstracts of the 61st*

(List continued on next page.)

OTHER PUBLICATIONS

*Scientific Sessions,* Supplement II Circulation, vol. 78, No. 4, Oct. 1988, at 220.

David M. Salerno, et al. "The Effect of Post-Resuscitation Hypokalemia on Ventricular Fibrillation Threshold in Dogs," *Abstracts of the 61st Scientific Sessions,* Supplement II Circulation, vol. 78, No. 4, Oct. 1988, at 237.

John Schuder, Ph.D., et al. "Superiority of Biphasic Shocks in the Defibrillation of Dogs via Epicaridal Patches and Catheter Electrode," Abstract, *Journal of the American College of Cardiology,* vol. 11, No. 2, Feb. 1988, at 58A.

John C. Schuder, et al. "Optimal Biphasic Waveform Morphology for Canine Defibrillation With a Transvenous Catheter and Subcutaneous Patch System," *Abstracts of the 61st Scientific Sessions,* Supplement II Circulation, vol. 78, No. 4, Oct. 1988, at 219.

Nestor G. Sepulveda, Ph.D., et al. "New Defibrillation Electrode Configurations: A Mathematical Prediction," *Presentation for American College of Cardiology,* Mar. 8-12, 1987.

Nestor G. Sepulveda, Ph.D., et al. "The Importance of Patch Electrode Pacement and Size On Defibrillation: a Finite-Element Analysis, etc. . . . " Abstract, *Journal of the American College of Cardiology,* vol. 11, No. 2, Feb. 1988, at 57A.

Nestor G. Sepulveda, Ph.D., et al. "Electrical Behavior of a Cardiac Bisyncytium during Defibrillation," *Journal of the American College of Radiology,* vol. 11, No. 2, Feb. 1988, at 58A.

Arjun D. Sharma, et al. "Right Ventricular Pressure during Ventricular Fibrillation in Man: Potential Implications for Implantable Antitachycardia Devices," *Abstracts of the 61st Scientific Sessions,* Supplement II Circulation, vol. 78, No. 4, Oct. 1988, 220.

Igor Singer, MBBS, FRACP, et al. "Pathologic Findings Related to the Lead System and Repeated Defibrillations in Patients With the Automatic Implantable Cardioverter-Defibrillators," *Journal of the American College of Cardiology,* vol. 10, No. 2, Aug. 1987, at 382-388.

Anthony S. L. Tang, M.D., et al. "Use of Gradient Maps to Create an Electrode Configuration with a More Even Defibrillation Field," Abstract, *Journal of the American College of Cardiology,* vol. 13, No. 2, Feb. 1989, at 66A.

Anthony S. L. Tang, et al. "Gradient Shock Fields from Intra-Cardiac Catheter & Cutaneous Patch," *Abstracts of the 61st Scientific Sessions,* Supplement II Circulation, vol. 78, No. 4, Oct. 1988, at 45.

R. K. Thakur, et al. "Clinical Cardiology: Implantable Defibrillators," *Abstracts of the 61st Scientific Sessions,* Supplement II, vol. 78, No. 4, Oct. 1988.

Gordon Tomaselli, M.D., et al. "The Technique of Automatic Implantable Cardioversion/Defibrillation," *The Journal of Critical Illness,* Feb. 1988, at 87-95.

Hans-Joachim Trappe, et al. "Evaluation of Global and Regional Left Ventricular Function Using Two-Dimensional and M-Mode Echocardiography in Patients Wtih an Automatic Implantable Cardioverter Difibrillator," *PACE,* vol. 11, Jul. 1988, at 1070-1076.

Paul J. Troup, et al. "Clinical Features of AICD System Infections," *Abstracts of the 61st Scientific Sessions,* Supplement II Circulation, vol. 78, No. 4, Oct. 1988, at 155.

Nicholas G. Tullo, M.D., et al. "Technological Improvements in Future Implantable Defibrillators," *Cardio,* May 1990, at 107-111.

James Vetter, M.D., et al. "Optimizing Biphasic Nonthoracotomy Internal Defibrillation," *Journal of the American College of Cardiology,* vol. 11, No. 2, Feb. 1988, at 57A.

Joseph T. Walls, M.D., et al. "Adverse Effects of Permanent Cardiac Internal Defibrillator Patches on External Defibrillation," *The American Journal of Cardiology,* vol. 64, Nov. 15, 1989, at 1144-1147.

Roger A. Winkle, M.D., et al. "Measurement of Cardioversion/Defibrillation Thresholds in Man By a Truncated Exponential Waveform and an Apical Patch-Superior Vena Caval Spring Electrode Configuration," *Circulation,* vol. 69, No. 4, Apr. 1984, at 766-771.

Roger A. Winkle, M.D., et al. "Practical Aspects of Automatic Cardioverter/Defibrillator Implantation," *American Heart Journal,* Nov. 1984, at 1335-1346.

Roger A. Winkle, M.D., FACC, et al. "Comparison of Defibrillation Efficacy in Humans using a New Catheter and Superior Vena Cava Spring-Left Ventricular Patch Electrodes," *Journal of the American College of Cardiology,* vol. 11, No. 2, Feb. 1988, at 365-370.

Roger A Winkle, et al. "Clinical Feasibility of an Automatic Combined Antitachcardia Device," *Abstracts of the 61st Scientific Sessions,* Supplement II Circulation, vol. 78, No. 4, Oct. 1988, at 220.

(List continued on next page.)

OTHER PUBLICATIONS

Seitaro Yabe, et al. "Effect of Strong Shock Fields on Activation Propagation Near Defibrillation Electrodes," *Abstracts of the 61st Scientific Sessions,* Supplement II Circulation, vol. 78, No. 4, Oct. 1988, at 154.

Raymond Yee, et al. "Sequential Pulse Countershock Between Two Transvenous Catheters: Feasibility, Safety, and Efficacy," *PACE,* vol. 12, Dec. 1989, at 1869–1877.

Raymond Yee, et al. "A Randomized Double Blind Study Comparing Single Versus Dual Chamber Pacing: Patient Preference and Effects on Functional Capacity," *Abstracts of the 61st Scientific Sessions,* Supplement II Circulation, vol. 78, No. 4, Oct. 1988, at 45.

Xiaohong Zhou, et al. "Importance of the Shock Electric Field for Defibrillation Efficacy," *Abstracts of the 61st Scientific Sessions,* Supplement II Circulation, vol. 78, No. 4, Oct. 1978, at 219.

DEFIBRILLATOR AND DEMAND PACER CATHETERS AND METHODS FOR USING SAME

RELATED APPLICATIONS

This patent application is a continuation-in-part of U.S. patent application Ser. No. 07/683,450, filed Apr. 10, 1991, now abandoned, in the name of Leo Rubin and entitled "Defibrillator and Demand Pacer Catheter and Method For Implantation."

BACKGROUND

1. Field of the Invention

The present invention relates to systems for regulating the contraction of a heart and more particularly to defibrillator and demand pacer catheters.

2. Background Art

The heart is a large hollow muscle used to pump blood to all parts of the body. Veins bring blood to the heart while arteries carry blood away from the heart. Valves control the flow of blood through the heart. The function of blood is to carry oxygen to the body parts. If the heart stops, the oxygen is no longer delivered and the body dies.

A muscle wall known as the septum divides the heart lengthwise into a right side and a left side. Each side has two chambers, one above the other. The upper chamber on the right side is the right atrium. The right atrium collects blood from the body through the veins. When the right atrium is full, a valve known as the tricuspid valve opens, providing a passage to the lower chamber. The muscle tissue surrounding the right atrium then contracts, pushing the blood into the lower chamber.

The lower chamber is called the right ventricle. Once the tricuspid valve closes, the muscle tissue surrounding the right ventricle contracts, pushing the blood to the lungs. The lungs provide oxygen that is absorbed into the blood. The blood then flows to the left side of the heart where it passes through a left atrium and a left ventricle, finally being ejected from the left ventricle to circulate through the body.

The heart has a special system of muscles that cause the heart tissue to regularly and continuously contract. One part of the system called the S-A node regularly emits electrical signals or pulses that travel through the heart tissue to a second point in the heart called the A-V node. The heart tissue contracts in response to the electrical pulses. A second part of the system called the bundle of His regulates the electrical pulses. The bundle of His insures that all muscle tissue surrounding a specific compartment simultaneously contracts and that the atriums and ventricles contract at the appropriate time. One complete contraction of both the ventricles and the atriums constitutes a beat.

On occasion, the electrical pulses being carried through the heart tissue become irregular, causing the heart to beat rapidly or unevenly. Defibrillation is a process used to restore normal beating to a heart in this condition. To defibrillate a heart, a large electrical charge called an electrical defibrillation pulse is applied directly to the heart. This electrical defibrillation pulse works to depolarize the electrical pulses of the heart and, thereby, restore normal beating.

There are other occasions in which the heart fails to deliver a specific electrical pulse, thereby causing the heart to pause, skipping a beat. Demand pacing is a process used to maintain normal beating of a heart in this condition. To demand pace a heart, sensors are used to determine if the heart is delivering its electrical pulses at the appropriate time. If the heart is not, a relatively small electrical charge called an electrical demand pacing pulse is applied directly to the heart to assist in electrical depolarization of the heart tissue. Individuals having heart problems often suffer from both of the above conditions and, thus, are benefited if they can receive both defibrillation and demand pacer pulses.

The electrical pulses for defibrillation and demand pacing are typically delivered to the heart through different methods. The defibrillation pulse has historically been delivered through a large area electrical patch sewn to the exterior surface of the heart. The electrical patch is connected to a capacitor that is charged by a battery, thereby to be capable of delivering an electrical defibrillation pulse. Once the capacitor discharges the defibrillation pulse, it enters directly into the heart of the patient so as to defibrillate the heart. The pulse then exits the body through a ground electrode attached to the skin of the patient.

Attaching the electrical patch to the heart of the patient requires an extensive operation in which the rib cage is separated so as to expose the heart. Once the heart is exposed, the patch can be sewn to the exterior surface. The surface area of the electrical patch must be of a sufficient size to deliver the high energy defibrillation pulse without burning the tissue of the heart. A typical electrical patch has a surface area in the range of about 50 $cm^2$ to about 100 $cm^2$, and is capable of delivering a defibrillation pulse with an energy of up to about 50 joules.

In contrast, the demand pacing pulses are often applied to the heart by a demand pacer catheter. The demand pacer catheter is a long flexible probe, usually made of stilastic or polyurethane, with electrical leads running the length of the catheter at the middle thereof. At one end of the probe, the leads are connected to an exposed metal surface called a demand pacer electrode. Part way up the probe, the leads are connected to a second exposed metal surface called a ground electrode. Finally, at the other end of the probe, the leads are connected to a regulator that has a controller for sensing the beat of the heart and a capacitor charged by a battery, for sending the demand pacer pulses to the heart.

The demand pacer catheter is used by making an incision in a vein leading to the heart. The end of the probe with the demand pacer electrode is inserted into the vein and threaded to the heart and into the right ventricle. When the heart delivers its electrical pulse to the muscle tissue, the signal is carried up the lead wires in the probe and to the controller. If the heart fails to deliver its electrical pulse, the controller senses the missing signal and tells the capacitor to transmit the electrical demand pacer pulse to the demand pacer electrode. Once emitted from the electrode, the pulse travels through the blood in the right atrium and into the surrounding heart tissue, thereby causing depolarization of the heart. The pulse finally leaves the body through the ground electrode.

In one version of the demand pacer catheter, the demand pacer electrode has a helical or corkscrew-shaped electrode for attachment to the interior of the heart. Such corkscrew-shaped electrodes typically have a length of about 5 mm with a surface area of about 6 $mm^2$. Furthermore, such electrodes are only capable of delivering an electrical current of about 5 milliamperes.

The trouble with the above-discussed approaches for applying the different electrical pulses is that two procedures are required: One for inserting the demand pacer catheter and one for attaching the defibrillator electrical patch. Furthermore, attaching the electrical patch is an extensive operation, exposing the patient to high risk conditions and requiring a long recovery period.

Attempts have been made to solve the above problems by producing a single catheter that can be inserted into the heart for applying both defibrillation and demand pacer pulses. One such catheter is an implantable, self-contained system for sensing the pulse of a heart and for automatically sending a defibrillator or demand pacer pulse to the heart depending on the condition of the heart. An example of such a catheter is found in U.S. Pat. No. 3,857,398 issued to Leo Rubin of the present invention.

Similar to the demand pacer electrode previously discussed, this catheter has a flexible probe that can be inserted into a vein and threaded through the right atrium and into the right ventricle of the heart. A ground electrode and a demand pacer electrode are attached to the portion of the probe in the right ventricle. A defibrillator electrode is attached to the portion of the probe in the right atrium. Connected to the other end of the probe is a regulator having a controller for sensing and analyzing the electrical pulse of the heart. The regulator further includes a defibrillator capacitor and demand pacer capacitor for transmitting their respective pulses to the heart. The capacitors are charged by a battery also located in the regulator. The regulator is inserted into the body, such as in the subcutaneous tissue of the chest wall, so that the system is independently contained within the body.

As the heart produces its electrical signal, the pulse is transferred through the probe and back to the controller. The controller then uses this information to determine if the heart is beating properly. If not, the controller automatically informs either the demand pacer capacitor or defibrillator capacitor to transmit its respective pulse to its respective electrode. The pulses then travel through the blood and into the surrounding heart tissue, thereby defibrillating or demand pacing the heart. Finally, the charge leaves the body by the ground electrode.

One of the dilemmas associated with the above-described invention is that it is much easier for electricity to travel through blood than it is for electricity to travel through heart tissue. As a result, a majority of the defibrillation pulse, which is delivered in the blood, travels directly to the ground electrode through the blood, rather than entering the heart tissue. Accordingly, the heart is not defibrillated. Attempts have been made to resolve this problem by increasing the energy of the defibrillation pulse. Such an alternative, however, has additional drawbacks.

Blood is predominantly made of water. In turn, water molecules are made of hydrogen and oxygen. Passing a high electrical current through water breaks down the water molecules to form hydrogen and oxygen gas bubbles. This is a process known as electrolysis. Studies have found that excessively high defibrillation pulses can result in the electrolysis of the blood, thereby forming hydrogen and oxygen gas bubbles within the heart. Such gas bubbles can build up enough pressure within the heart to tear the heart tissue.

Furthermore, raising the strength of the defibrillation pulse increases the risk to the patient. If one defibrillation pulse should conduct better than another, an excessively high defibrillation pulse could result in damage to the heart tissue.

Finally, increasing the size of the defibrillation pulse requires a larger capacitor to deliver the pulse which in turn increases the size of the regulator. Also, use of a larger capacitor requires either a larger battery to be implanted or an increase in the frequency in which the battery must be replaced by implanting a new regulator. Such options increase the inconvenience to the patient.

Another troubling aspect is that it is difficult to target a specific charge with the previous defibrillator and demand pacer catheters. At times, it may be beneficial to direct a defibrillation or demand pacer pulse to a specific point in the heart. The previous catheters are free-floating within the heart. Therefore, they shift position with the movement of the patient or the beat of the heart. Hence, it is difficult to target the pulse.

Accordingly, some of the problems associated with the previous catheters used to defibrillate and demand pace the heart include: multiple and complex operations to attach the required electrodes, the necessity to use excessively high energy pulses that result in gas bubbles and increased threat to the patient, and the inability to strategically target a pulse for optimal effect.

BRIEF SUMMARY AND OBJECTS OF THE INVENTION

Accordingly, it is an object of the present invention to provide methods and apparatus for regulating the beating of a heart.

It is another object of the present invention is to provide a single apparatus that can effectively deliver both defibrillator and demand pacer pulses to a heart.

Yet another object of the present invention to provide apparatus as above that can be inserted in a single surgical procedure.

Still another object of the present invention is to provide apparatus and methods to effectively deliver a defibrillation pulse to the heart without causing electrolysis of the blood.

Also, another object of the present invention is to provide an apparatus that effectively delivers a defibrillation pulse while minimizing the threat of injury to the patient or the heart tissue.

It is yet another object of the present invention to provide an apparatus as above that can be selectively positioned in the heart to target a defibrillator or demand pacer pulse.

Furthermore, an additional object of the present invention is to minimize the capacitor size necessary to operate the above apparatus.

Finally, it is an object of the present invention to maximize the life span of the battery used to operate the above apparatus so as to minimize replacement of the battery.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a catheter capable of delivering defibrillator and demand pacer pulses to the heart is provided. The catheter comprising an elongated probe having a distal end that can be positioned in a ventricle of the heart. Longitudinally disposed within the probe is an electrically conducted pathway capable of delivering electrical signals, including a defibrillation pulse and a demand pacer pulse, through the probe. A defibrillator electrode projects from the distal end of the probe and is electrically coupled with the electrically conductive pathway. The defibrillator electrode is structured to deliver at least a portion of a defibrillation pulse directly to the interior of the septum of the heart.

Attached to the probe at a distance from the defibrillator electrode is a demand pacer electrode. The demand pacer electrode is insulated from the defibrillator electrode and is electrically coupled with the electrically conducted pathway to deliver an electrical demand pacer pulse to the heart. To receive the defibrillator and demand pacer pulses after they are delivered to the heart, a ground electrode is attached to the probe at a distance from the distal end. The ground electrode is also coupled with the electrically conducted pathway.

In a preferred embodiment, the defibrillator electrode is a helix that can be screwed into the interior of the septum of the heart. The helix has a length in the range of about 0.5 cm to about 1.0 cm and an electrical surface area of at least 1.2 cm$^2$. The electrical surface area must be sufficient to deliver an electrical defibrillation pulse of up to about 50 joules without burning the surrounding tissue.

In one embodiment, the helix is inserted into the heart tissue by rotating the entire catheter. In an alternative embodiment, the helix is independently rotated for insertion into the septum.

It is also envisioned that the defibrillator electrode is a lance with barbs. The lance is inserted into the heart tissue by a spring gun that propels the lance and embeds it into the interior of the septum. To facilitate insertion and removal of the lance into the septum, the barbs are structured to selectively retract into the lance.

In another embodiment, a supplemental defibrillator electrode is attached to the probe at a distance from the distal end. The supplemental defibrillator electrode is electrically coupled to the defibrillator electrode and to the electrically conducted pathway such that the defibrillation pulse is delivered simultaneously through both the defibrillator electrode and the supplemental defibrillator electrode.

The present invention also provides for a system for regulating the beating of a heart. The system includes the catheter as previously discussed attached to a regulator at the proximal end of the probe. In the preferred embodiment, the regulator includes a controller, a defibrillator circuit, and a demand pacer circuit. The controller senses and analyzes the electrical charge created by the heart. Depending upon the results of the analysis, the controller informs the demand pacer circuit or defibrillator circuit to discharge either a demand pacer pulse or a defibrillation pulse, respectively. The pulse then travels down the electrically conductive pathway of the catheter and is discharged to the heart through its respective electrode.

Finally, the present invention also provides for a method for regulating the beating of a heart. The method includes making an incision into a blood vessel leading to the heart. The distal end of the previously discussed catheter is then inserted into the blood vessel through the incision in the blood vessel. Once inserted, the catheter is threaded through an atrium of the heart and into a ventricle. The catheter is then attached to the heart by anchoring the defibrillator electrode to the septum. Preferably, this is accomplished by screwing the helical defibrillator electrode directly into the interior of the septum.

Electrical signals created by the heart are sensed by the controller attached to the catheter. The controller analyses these signals, and as previously discussed, informs the defibrillator circuit or demand pacer circuit to transmit their respective signal. These signals are carried through the probe and discharged from the respective electrodes to the heart. Finally, the pulses transmitted by the catheter leave the heart by entering the probe through the ground electrode.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENT

Figure 1:
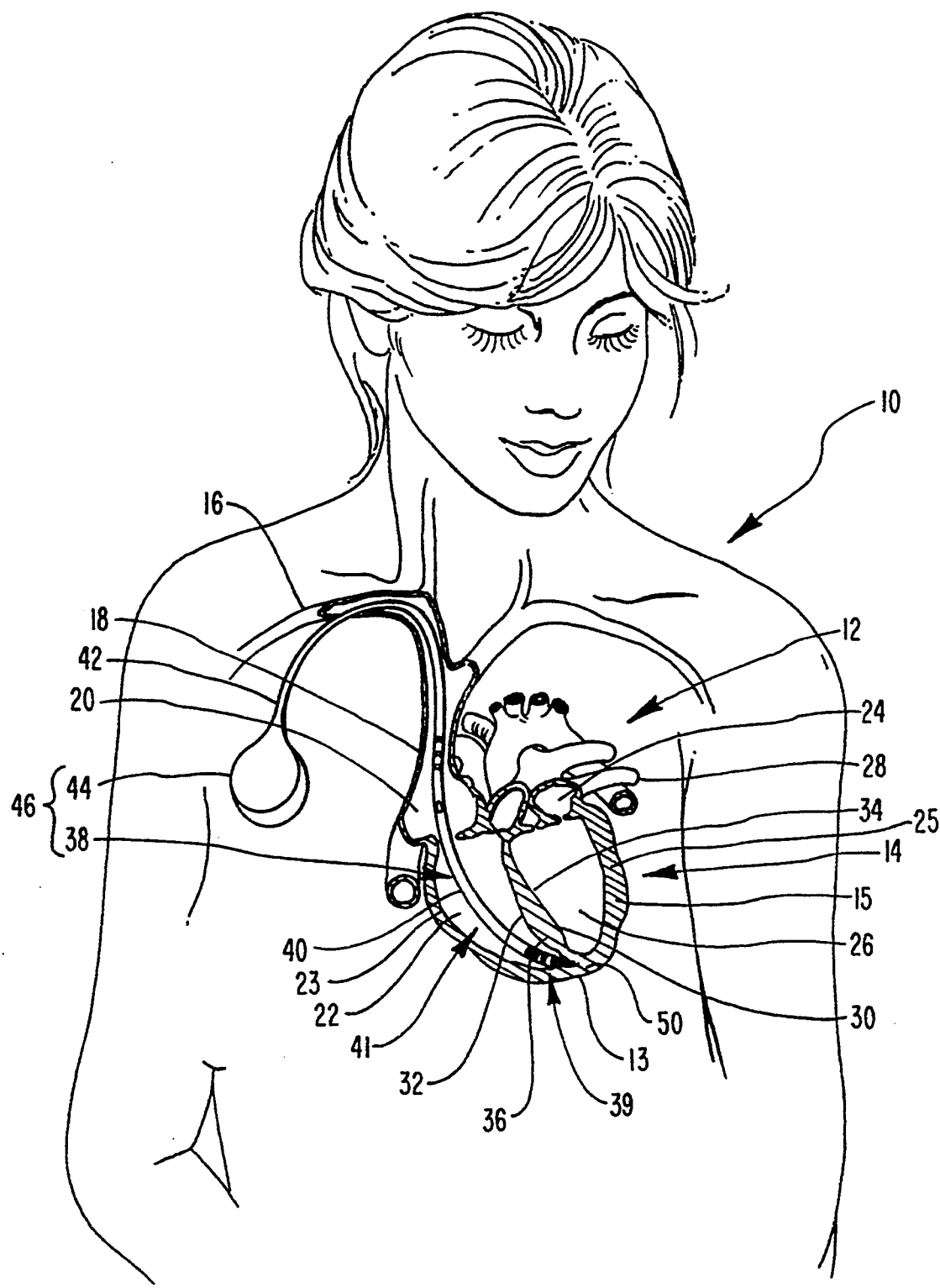
FIG. 1 is a perspective view of the inventive defibrillator and demand pacer system implanted in the heart and chest of a patient.

Referring to FIG. 1, a patient 10 is shown having a chest 12 with a heart 14 made of heart tissue 15 and defined by an exterior surface 13. A vein 16 enters a right atrium 20 of heart 14 through the superior vena cava 18. Right atrium 20 communicates with a right ventricle 22. Heart 14 further comprises a left atrium 24 communicating with a left ventricle 26. In turn, left ventricle 26 feeds into an artery 28 which leads away from heart 14. Right ventricle 22 and left ventricle 26 are separated from chest 12 by an exterior right ventricle wall 23 and an exterior left ventricle wall 25, respectively. Right ventricle 22 is separated from left ventricle 26 by a septum 30. Septum 30 has an outer wall 32 in right ventricle 22 and an outer wall 34 in left ventricle 26. The portion of septum 30 between outer walls 32 and 34 defines an interior 36 of septum 30.

Disposed within heart 14 is a catheter 38 comprising an elongated, flexible, electrically non-conductive probe 39 having a proximal end 42 and a distal end 40 that terminates in a tip 41. Electrically coupled and attached to proximal end 42 of probe 39 is a regulator 44. Catheter 38 and regulator 44 comprise a system 46 that is capable of controlling the beat of heart 14 of patient 10 by delivering electrical signals, including an electrical defibrillation pulses and an electrical demand pacer pulses, to heart 14.

Figure 2:
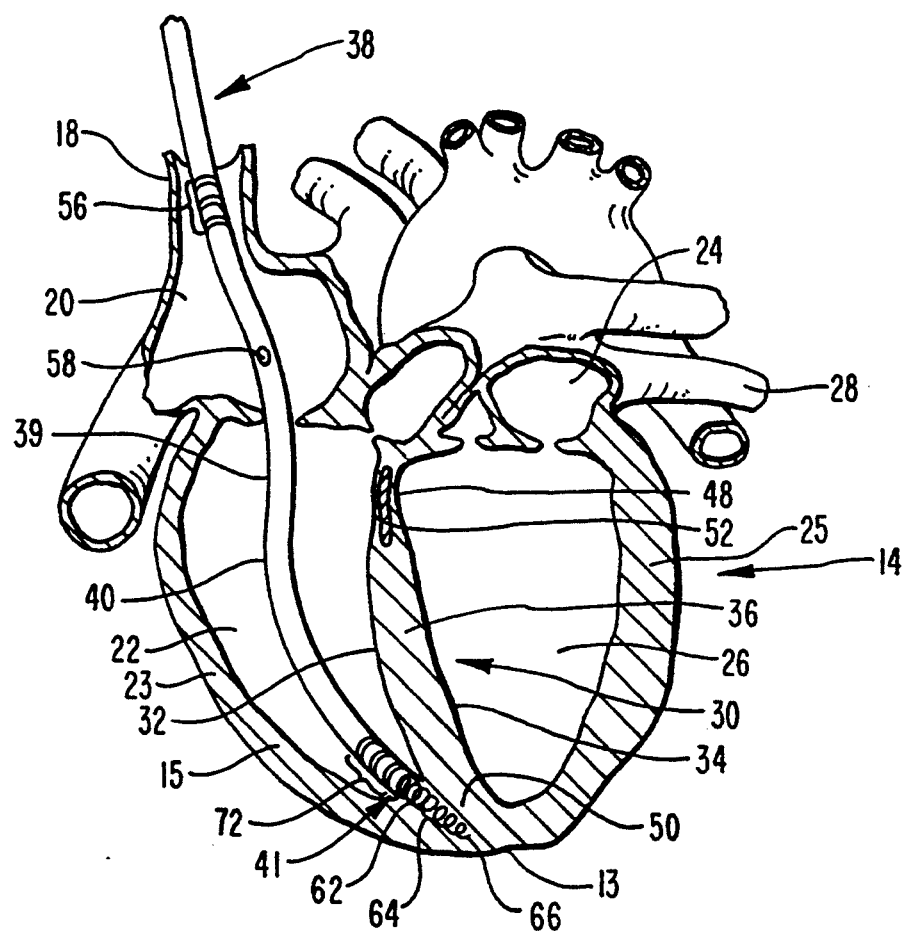
FIG. 2 is an enlarged view of the distal end of the catheter shown in FIG. 1, including a first embodiment of a helical defibrillator electrode anchored into the muscular section of the septum.

Depicted in FIG. 2 is an enlarged view of distal end 40 of catheter 38 disposed in heart 14. The figure shows septum 30 having a membranous section 48 near the atriums of the heart 14 and a muscular section 50 at the opposing end of septum 30. Muscular section 50 includes heart tissue 15 located at the intersection of exterior left ventricle wall 25 and exterior right ventricle wall 23 and extends to exterior surface 13. The width of septum 30 varies from about 0.7 cm to about 1.2 cm with the widest part being at muscular section 50. Positioned near membranous section 48 of septum 30 in interior 36 is the bundle of His 52. Bundle of His 52 functions to regulate the electrical pulses from heart 14 that travel through heart tissue 15 to contract heart 14.

Catheter 38 is further depicted in FIG. 2 as comprising ground electrode 56, exit port 58, and supplemental defibrillator electrode 72. These features shall be discussed later in detail. In accordance with the present invention, however, there is also provided defibrillator means for anchoring probe 39 to septum 30 and for transmitting at least a portion of an electrical defibrillation pulse directly to interior 36 of septum 30. By way of example and not by limitation, FIG. 2 shows a defibrillator electrode 62 being a helix 64 that projects from tip 41 of probe 39 and terminates in a point 66. By rotating helix 64, it is advanced into interior 36 of septum 30, thereby anchoring probe 39 to septum 30 and enabling the delivery of a defibrillation pulse directly to interior 36. Alternative embodiments include defibrillator electrode 62 being a spike or a spear that can be inserted into septum 30. Specific alternative embodiments for the defibrillator means will be disclosed later.

To defibrillate heart 14, a critical mass of heart tissue 15 must be depolarized by the defibrillation pulse. It has been discovered that heart tissue 15 located in interior 36 of septum 30 has higher electrical conductivity than surrounding heart tissue 15. Accordingly, by delivering an electrical defibrillation pulse directly to interior 36, less energy is required to defibrillate heart 14. Hence, the safety of patient 10 is increased since the probability that electrolysis of the blood will occur or that heart tissue 15 will be burned is decreased.

Figure 3:
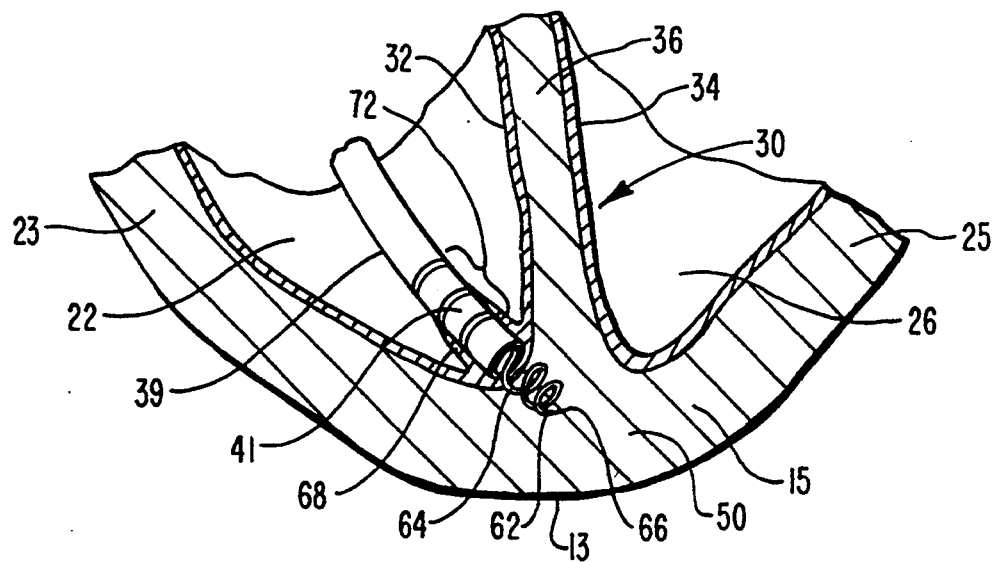
FIG. 3 is an enlarged view of the helical defibrillator electrode anchored into the muscular section of the septum as shown in FIG. 2, including a depiction of the tissue lining on the inner walls of the heart.

Optimal insertion of defibrillator electrode 62 should be within septum 30 to take advantage of the highly conductive heart tissue 15 in interior 36 but should be as far away as possible from bundle of His 52 so as not to disrupt its function of regulating the heart. Ideally, defibrillator electrode 62 is inserted into muscular section 50 of septum 30 as shown in FIG. 3. This positioning has the additional advantage of using the widest portion of septum 30 which provides more area for defibrillator electrode 62 to be inserted into. At a minimum, defibrillator electrode 62 should be inserted 5 cm from bundle of His 52. How defibrillator electrode 62 is inserted in septum 30 will be discussed later. FIG. 3 further depicts a tissue layer 68 residing in heart 14. Over a period of time, tissue layer 68 bonds to and grows on catheter 38. In turn, this bonding effect increases the ability of the defibrillation pulse to flow through heart tissue 15.

Figure 4:
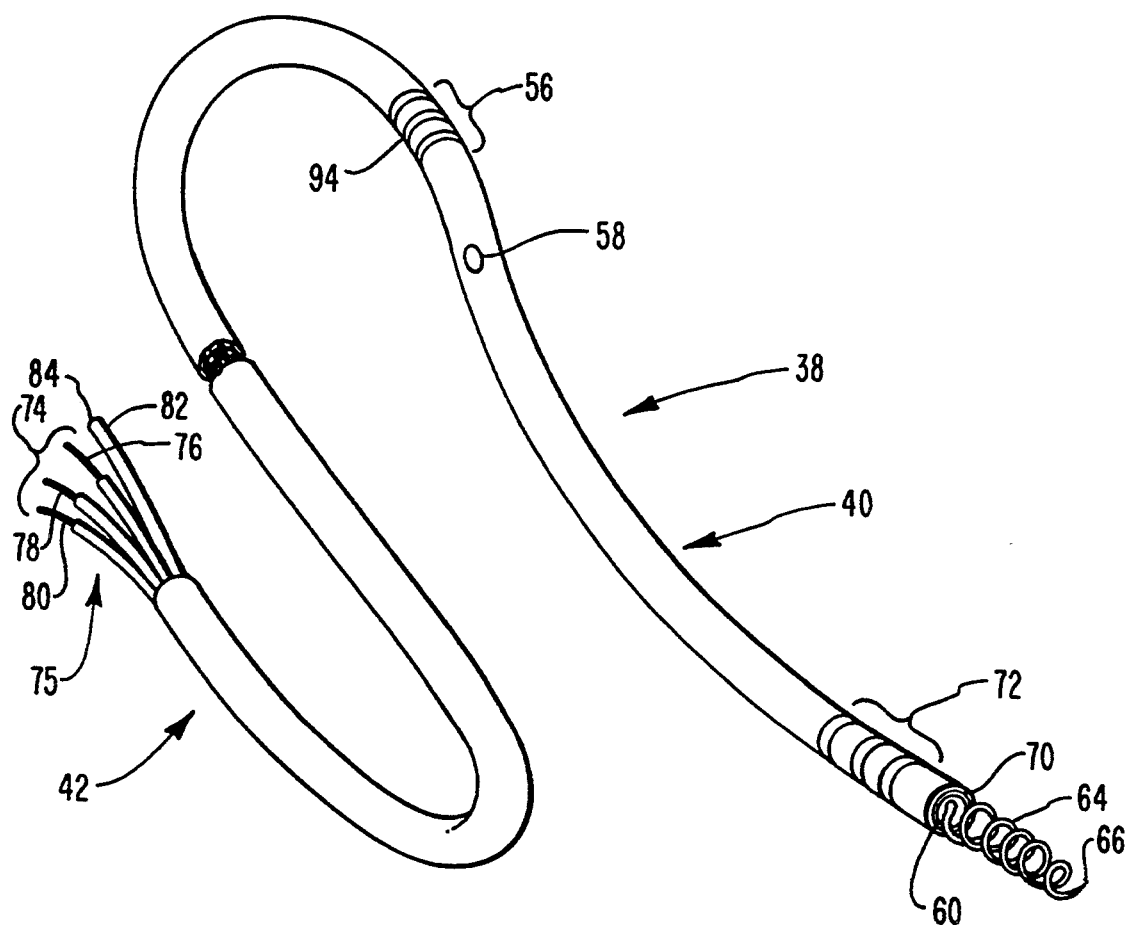
FIG. 4 is a perspective view of the inventive defibrillator and demand pacer catheter showing lead wires projecting from a probe and showing a defibrillator electrode, supplemental defibrillator electrode, demand pacer electrode and a ground electrode attached to the probe.
Figure 5:
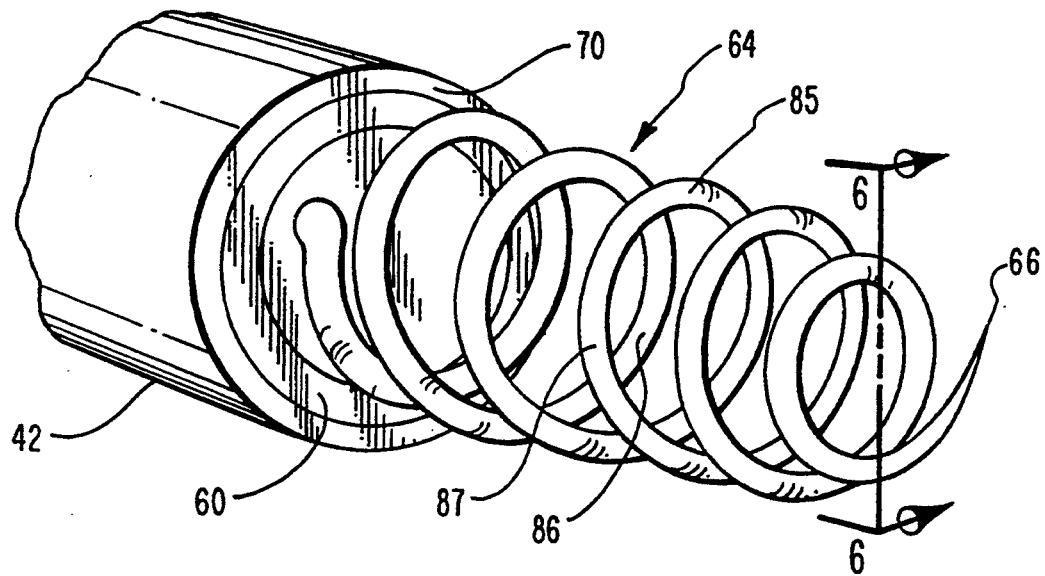
FIG. 5 is an enlarged view of the helical defibrillator electrode centrally projecting from the tip of the probe, the demand pacer catheter encircling the defibrillator electrode.

The embodiments shown in FIGS. 4 and 5 reveal probe 39 having an end face 70 located at tip 41 of probe 39. Attached to end face 70 is a demand pacer electrode 60 capable of delivering a demand pacer pulse and positioned a distance from defibrillator electrode 62 so as to be insulated therefrom. Also shown in FIG. 4 is supplemental defibrillator electrode 72 which is electrically coupled with defibrillator electrode 62 and is capable of delivering an electrical defibrillation pulse.

Electrical signals are delivered to their respective electrodes by an electrically conductive pathway 74 longitudinally disposed within probe 39 from proximal end 42 to distal end 40. Electrically conductive pathway 74 has a first end 75 depicted in FIG. 4. Electrically conductive pathway 74 includes ground lead 76 electrically coupled with ground electrode 56, demand pacer lead 78 electrically coupled with demand pacer electrode 60, and defibrillator lead 80 electrically coupled with both supplemental defibrillator electrode 72 and defibrillator electrode 62. In an alternative embodiment, defibrillator lead 80 is electrically coupled only with defibrillator electrode 62. All leads and electrodes are insulated and separated from one another so as not to produce an electrical short. Furthermore, in the preferred embodiment all leads are made of a material having a low impedance, typically less than 10 Ohms so as to minimize energy loss. Also shown at proximal end 42 of probe 39 is atrial lumen 82 having a receiving port 84. The function of atrial lumen 82 shall be discussed later.

Catheter 38 of FIG. 4 is operative in several modes. In the first mode, catheter 38 acts independently as a defibrillator. To defibrillate heart 14, a defibrillation pulse is transmitted down defibrillator lead 80 where it is discharged from defibrillator electrode 62 into interior 36 of septum 30. A defibrillation pulse is typically in a range between about 0.5 joules to about 50.0 joules. Accordingly, for defibrillator electrode 62 to be effective, defibrillator electrode 62 must be capable of delivering such a charge without injury to itself or the immediate surrounding heart tissue 15.

To accomplish this, defibrillator electrode 62 is provided with an electrical surface area 85 that is large enough to uniformly deliver the electrical defibrillation pulse to interior 36 of septum 30 at levels low enough not to burn heart tissue 15. Defibrillator electrode 62 has an electrical surface area 85 in the range of about 1.2 centimeters squared to about 2.0 centimeters squared. Such an area generally requires that defibrillator electrode 62 have a length in a range of about 0.5 centimeters to about 1.0 centimeter and that helix 64 have a thickness in a range of about 7 French (cm) to about 11 French (cm).

Figure 6:
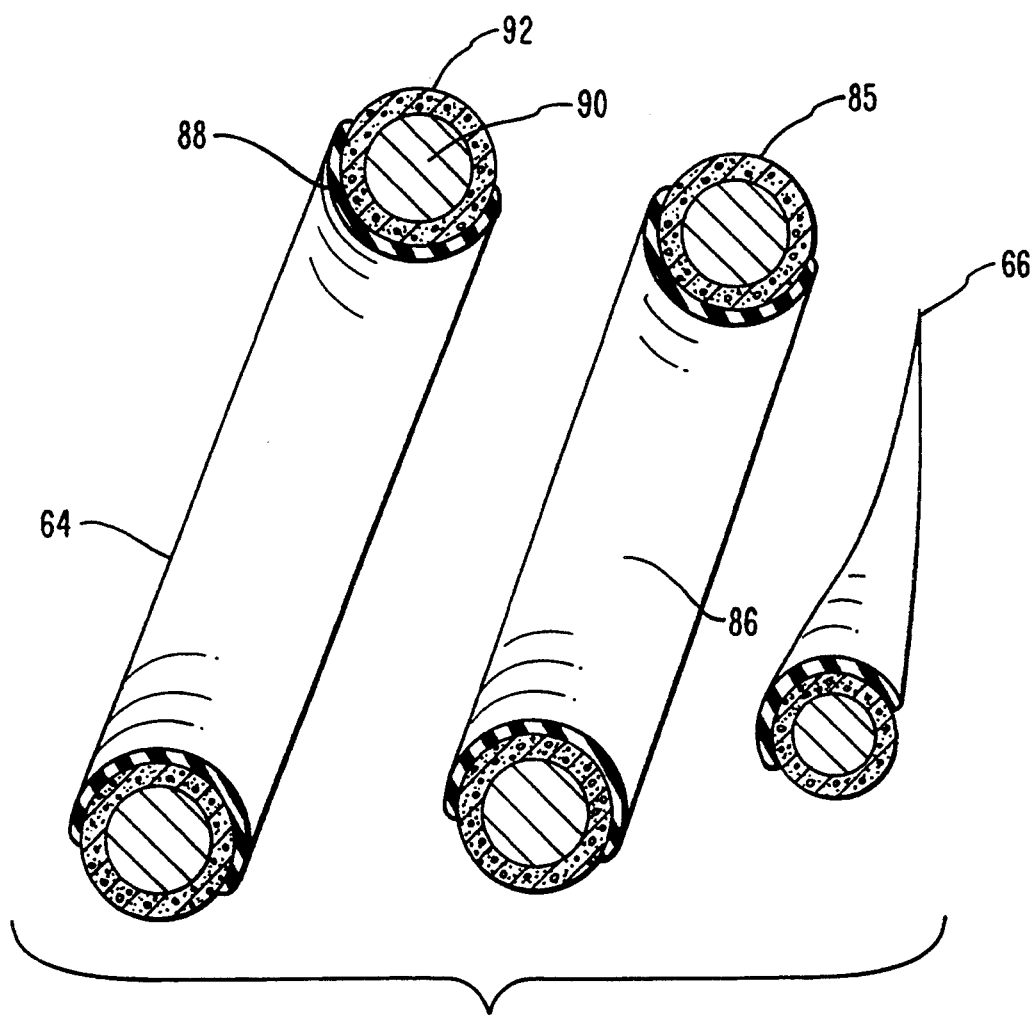
FIG. 6 is a cross-sectional view of the last three turns of the helix in FIG. 5, including a depiction of the core, porous surface, and insulation coating of the helix.

Delivering a defibrillation pulse through helix 64 provides additional concerns. Helix 64 as shown in FIG. 5 has an interior surface 86 that faces the center of helix 64 and an exterior surface 87 that faces away from the center of helix 64. Due to the shape of helix 64, as the defibrillation pulse passes through helix 64, heart tissue 15 located in the center of helix 64 is exposed to a much higher electrical pulse than heart tissue 15 surrounding helix 64. Accordingly, heart tissue 15 located in the center of helix 64 is easily damaged. The present invention however, provides an embodiment that resolves this problem. FIG. 6 depicts a cross sectional view of the last three turns of helix 64 used to deliver a defibrillation pulse. Attached to interior surface 86 is an insulated coating 88 which inhibits the delivery of the defibrillation pulse to heart tissue 15 within helix 64. Accordingly, all of the defibrillation pulse is delivered through exterior surface 87 of helix 64. With regard to the embodiment in FIG. 6, electrical surface area 85 thus constitutes exterior surface 87 of helix 64.

FIG. 6 also reveals that defibrillator electrode 60 comprises a core 90 surrounded by a porous surface 92. Core 90 is made of a highly conductive, non-corrosive metal such as titanium or platinum. Porous surface 92 is formed by sintering finely ground metal particles, generally titanium or platinum, to core 90. To produce porous surface 92, core 90 is roughened and then coated with a binder to which the particles adhere. After the binder has dried, core 90 is sintered at high temperatures in a reducing atmosphere to fuse the particles together and to the surface. The metal particles are thus joined together to form an interconnecting network of pores distributed uniformly through the coating. Porous surface electrodes are described in the *Journal of Thoracic and Cardiovascular Surgery*, St. Louis, Vol. 78, No. 2, pp. 281-291, August 1979, C. V. Mosby Company, authored by David C. MacGregor, et al.

The benefit of using porous surface 92 is that electrical surface area 85 of defibrillator electrode 62 is increased without substantially increasing the size of defibrillator electrode 62. By increasing the electrical surface area 85, a smaller defibrillator electrode 62 can be used to deliver the defibrillation pulse without injury to heart tissue 15. A smaller defibrillator electrode 62 is preferred as it is easier to install and is less damaging to heart 14 when inserted in septum 30.

Figure 7:
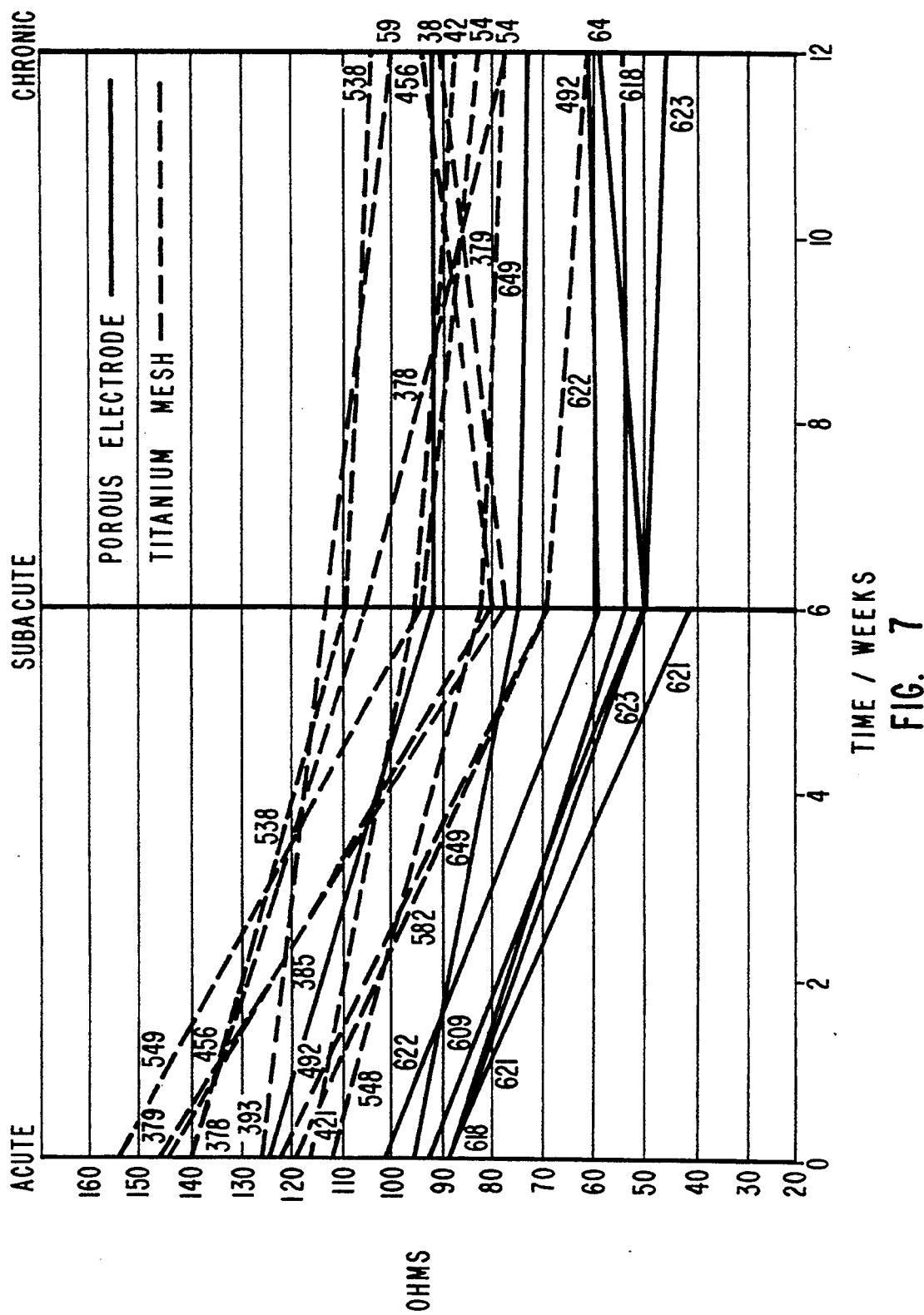
FIG. 7 is a graph of the interface resistivity between the inventive defibrillating electrode illustrated in FIGS. 1 through 6 and the heart tissue for two types of electrode materials during long-term implantation in non-human experimental subjects.

The use of porous surface 92 has also been found to reduce the electrical resistance of heart tissue 15 to the defibrillation pulse. The graph in FIG. 7 shows a comparison of the effect on the resistance of heart tissue 15 when defibrillator electrode 62 with different surfaces are inserted in non-human subjects over long periods of time. The study attached defibrillator electrode 62 with a porous surface 92 and defibrillator electrode 62 with a titanium mesh surface to a variety of non-human subjects. The electrical resistivity caused by heart tissue 15 in response to 500 volt, 6 millisecond defibrillation pulses was then measured over a twelve week period. The results are plotted on the graph in FIG. 7.

The Y-axis of the graph is the electrical resistance, measured in Ohms, caused by heart tissue 15; and the X-axis is time, measured in weeks. The solid lines are subjects using porous electrode while the dashed lines are subjects using titanium mesh electrodes. Each line has a number designating the non-human subjects. As is evidenced by the graph, the electrical resistivity caused by the heart tissue decreases over the first six weeks that the defibrillator electrode 62 is inserted. This is attributed to tissue grows onto the electrodes. After six weeks, the effectiveness of the growth by the tissue is minimized and the resistivity is generally constant.

Comparison of the porous and mesh electrodes reveals that, on average, the porous surface results in a much lower resistivity by heart tissue 15. The minimum electrical resistivity using the porous electrodes after six weeks was 40 Ohms while the minimal electrical resistivity using the titanium mesh electrodes after six weeks was 70 Ohms. Such a reduction in resistivity is attributed to the fact that the tissue is better able to grow into the porous surface electrodes, thereby enhancing contact with the tissue. Minimizing electrical resistivity in the heart tissue is beneficial since a lower charge can be used to effectively defibrillate heart 14.

After the electrical defibrillation pulse is delivered from defibrillator electrode 62 into interior 36 of septum 30, it travels through heart 14, leaving the body through ground electrode 56, thereby forming a complete circuit. Ground electrode 56 is shown in FIG. 4 as attached to probe 39 at a distance from tip 41. Typically, ground electrode 56 is positioned so as to reside in superior vena cava 18 when defibrillator electrode 62 is anchored into septum 30. This position requires the defibrillation pulse to travel the length of the heart 14 before it is able to exit the body, thereby maximizing the effect of the defibrillation pulse. In alternative embodiments, ground electrode 56 can be positioned independent of catheter 38 such as on the exterior of patient 10.

Similar to defibrillator electrode 62, ground electrode 56 has an electrical surface area, preferably porous, in a range of about 1.2 centimeters squared to about 2.0 centimeters squared. Likewise, ground electrode 56 is made from non-corrosive, high conductive metals, preferably titanium or platinum. In FIG. 4, ground electrode 56 is shown as comprising three ring electrodes 94 that are electrically connected in parallel with each other, each ring having a width in a range of about 4 millimeters to about 8 millimeters. A plurality of ring electrodes are preferred over a single ground electrode 56 since ring electrodes 94 permit greater flexibility of the probe and thus greater ease in inserting into heart 14.

Figure 8:
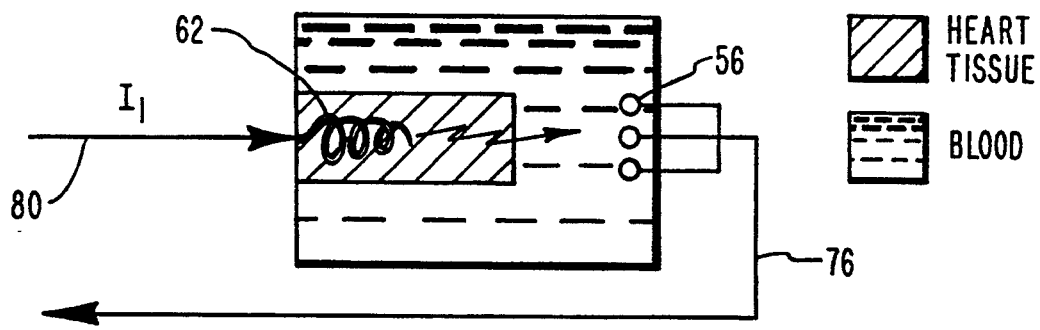
FIG. 8 is an electrical schematic diagram showing the defibrillation pulse traveling from the helical defibrillator electrode, through the heart tissue, into the blood and exiting the body through the ground electrode.

FIG. 8 provides a schematic electrical flow diagram for catheter 38 acting as a defibrillator. Electrical defibrillator current $I_1$ is transmitted down defibrillator lead 80 into defibrillator electrode 62 where it is discharged into interior 36 at septum 30. The current travels through heart tissue 15 defibrillating heart 14, and then travels into the blood where it enters ground electrode 56 and follows ground lead 76.

In an alternative embodiment for defibrillation, defibrillator lead 80 is also connected to supplemental defibrillator electrode 72 for simultaneously delivering the electrical defibrillation pulse from both defibrillator electrode 62 and supplemental defibrillator electrode 72. Supplemental defibrillator electrode 72 has the same structural description as ground electrode 56 and is shown in FIG. 4 as a plurality of ring electrodes positioned near tip 41 of probe 39. The benefit of using supplemental defibrillator electrode 72 is that since supplemental defibrillator electrode 72 delivers its portion of the defibrillation pulse in the blood, that portion of the pulse is delivered to a large area of heart tissue 15. Thereby, it effectively assists the portion of the defibrillation pulse delivered in septum 30 to defibrillate heart 14.

Figure 9:
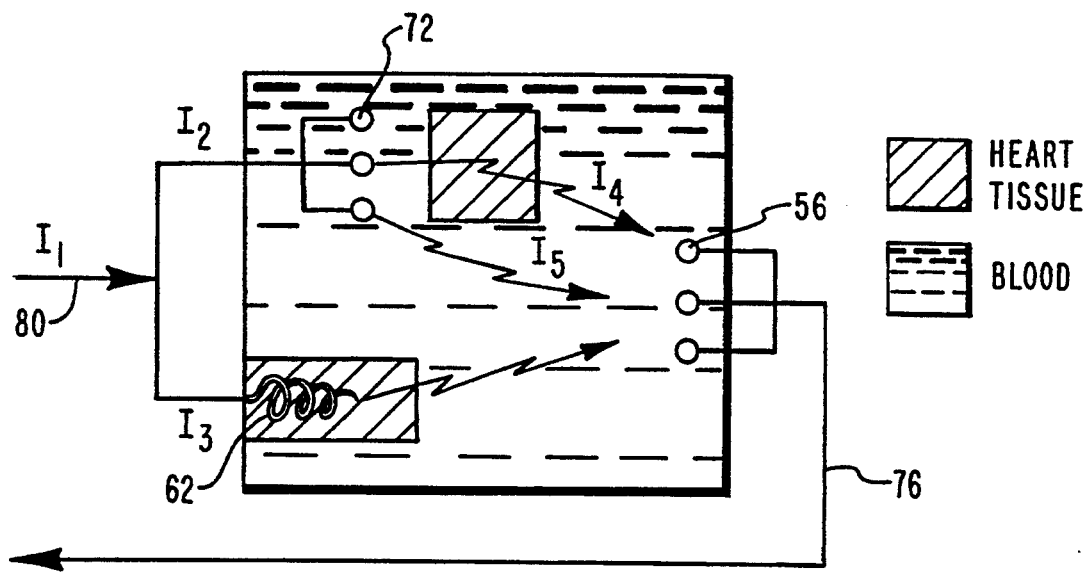
FIG. 9 is an electrical schematic diagram showing the path of the defibrillation pulse as it is simultaneously emitted from the helical defibrillator electrode, anchored in the septum, and the supplemental defibrillator electrode, attached to the side of the probe.

Depicted in FIG. 9 is a schematic electrical flow diagram in which supplemental defibrillator electrode 72 is used in combination with defibrillator electrode 62 to deliver the defibrillation pulse. Electrical defibrillation pulse $I_1$ travels down defibrillator lead 80 where it splits to form pulses $I_2$ and $I_3$. Pulse $I_2$ is delivered through supplemental defibrillator electrode 72 into the blood in right atrium 20. Once current $I_2$ is discharged, it follows two general paths. Pulse $I_4$ travels from the blood into the surrounding heart tissue and back into the blood where it enters ground electrode 56. In contrast, pulse $I_5$ travels directly through the blood to ground electrode 56 without entering heart tissue 15. Accordingly, $I_5$ does not assist in defibrillating heart 14. Pulse $I_3$ which is delivered through helix 64 has the same path as previously discussed. That is, $I_3$ is discharged from defibrillator electrode 62 in interior 36 of septum 30 where it travels through surrounding heart tissue 15 and into the blood, finally entering ground electrode 56. Once currents $I_3$, $I_4$, and $I_5$ enter ground electrode 56, they travel back up ground lead 76.

In an alternative method of operation, catheter 38 can function as a demand pacer. In this method of operation, a demand pacer pulse is delivered to demand pacer electrode 60. Demand pacer electrode 60 has an electrical surface area 96 in a range between about 0.4 mm$^2$ to about 10.0 mm$^2$ and is made of highly conductive, non-corrosive metals such as titanium or platinum. Electrical surface area 96 of demand pacer electrode 60 is significantly smaller than electrical surface area 85 of defibrillator electrode 62. This is due to the fact that the demand pacer pulse has a much smaller current requirement, typically in a range from about 0.1 milliampere to about 10.0 milliamperes, than the defibrillation pulse which can be as high as 10,000 milliamperes. Accordingly, demand pacer electrode 60 is not capable of functioning as defibrillator electrode 62 since the delivery of a defibrillation pulse through demand pacer electrode 60 would most likely destroy the electrode and burn the surrounding heart tissue 15.

In the preferred embodiment as shown in FIG. 5, demand pacer electrode 60 is positioned on end face 70 such that when defibrillator electrode 62 is anchored into septum 30 demand pacer electrode 60 is placed against outer wall 32 of septum 30. In such a position, the demand pacer pulse delivered from demand pacer electrode 62 is more efficient since more of the pulse is delivered directly into heart tissue 15.

Often, demand pacing is initiated immediately after defibrillation of heart 14. Studies have found, however, that tissue immediately adjacent to a defibrillator electrode requires a time period after receiving the defibrillation pulse before the tissue can effectively react to a demand pacer pulse. Accordingly, to permit demand pacing immediately following delivery of the defibrillation pulse, the demand pacer electrode 60 should be placed at least 3 millimeters away from the defibrillator electrode 62.

In an alternative embodiment, demand pacer electrode 60 can be positioned on probe 39 similar to supplemental defibrillator electrode 72. In such an embodiment, however, the demand pacer pulse is less efficient since it is required to first travel through the blood before entering the heart tissue. Accordingly, a larger percentage of the pulse travels directly to ground electrode 56 without ever entering the heart tissue 15.

Figure 10:
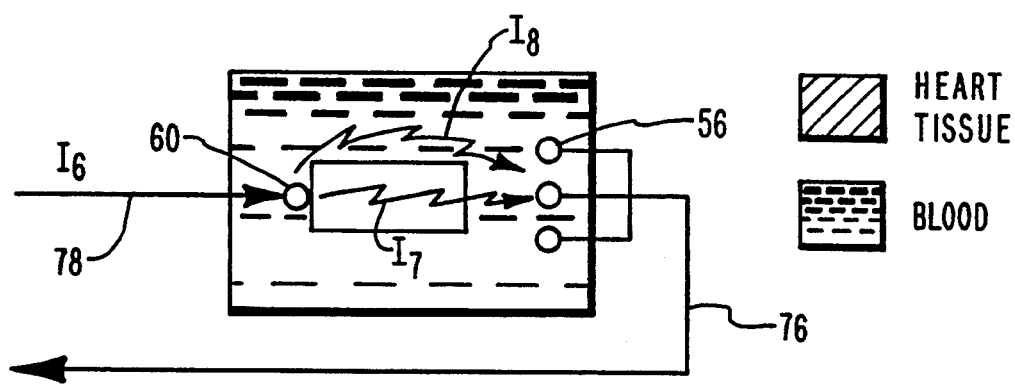
FIG. 10 is an electrical schematic diagram showing the path of the electrical demand pacer pulse as it is delivered from the demand pacer electrode to the side of the septum wall.

FIG. 10 is a schematic electrical flow diagram in which the demand pacer pulse is delivered through the demand pacer electrode 60 positioned on end face 70. In the flow diagram, demand pacer pulse $I_6$ travels down demand pacer lead 78 where it is discharged from demand pacer electrode 60 positioned against outer wall 32 of septum 30. Once $I_6$ is discharged, it travels in two paths. Pulse $I_7$, which is a majority of pulse $I_6$, travels directly into septum 30 and surrounding heart tissue 15. Pulse $I_7$ then travels into the blood and finally enters ground electrode 56. Pulse $I_8$, which is the remainder of pulse $I_6$, travels directly from demand pacer electrode 60 through the blood and into ground electrode 56. Once pulses $I_7$ and $I_8$ enter ground electrode 56, they travel up ground lead 76.

Figure 11:
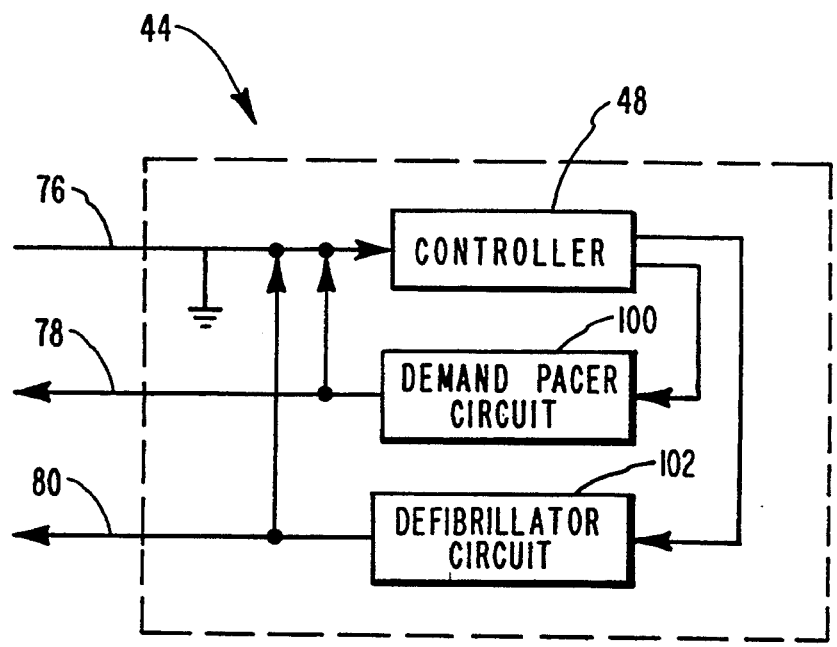
FIG. 11 is an electrical schematic diagram showing a regulator which includes a controller that senses the pulse from the heart and a demand pacer circuit and defibrillator circuit which discharge electrical pulses to the heart.

In accordance with the present invention, there is also provided governing means for sensing and analyzing the pulse of heart 14 and for emitting an electrical defibrillation pulse or an electrical demand pacer pulse depending on the results of the analyzing. By way of example and not limitation, there is shown in FIG. 11 regulator 44. Regulator 44 is electrically coupled with first end 75 of electrically conductive pathway 74. Regulator 44 comprises a controller 98, a demand pacer circuit 100, and a defibrillator circuit 102. FIG. 7 is a schematic electrical flow diagram of how regulator 44 functions with catheter 38.

As the heart produces its electrical signal, controller 98 senses an electrical potential either across ground lead 76 and demand pacer lead 78 or across ground lead 76 and defibrillator lead 80. In turn, controller 98 analyzes the electrical potential or the absence of such electrical potential and sends a signal to either demand pacer circuit 100 or defibrillator circuit 102 depending on the analysis.

When demand pacer circuit 100 receives a signal from controller 98, a capacitor within demand pacer circuit 100 transmits a demand pacer pulse to demand pacer lead 78 which travels to demand pacer electrode 60 as previously discussed. If defibrillator circuit 102 receives the signal from controller 98, a capacitor within defibrillator circuit 102 transmits a defibrillation pulse to defibrillator lead 80 which travels to defibrillator electrode 62 as previously discussed. The capacitors receive their energy from a power source located in controller 98. In an alternative embodiment, controller 98 can receive signals from sensors that are independent from catheter 38. For example, the sensors can be attached to the exterior of patient 10. Operation of regulator 44 is discussed in greater detail in U.S. Pat. No. 3,857,398 issued Dec. 31, 1974 to Leo Rubin and entitled "Electrical Cardiac Defibrillator" which is incorporated herein by specific reference.

In the embodiment shown in FIG. 1, regulator 44 is self-contained within patient 10, such as within the subcutaneous tissue of the chest wall. In an alternative embodiment, regulator 44 can be positioned outside of the patient for monitoring patients that are maintained in a hospital.

Figure 12:
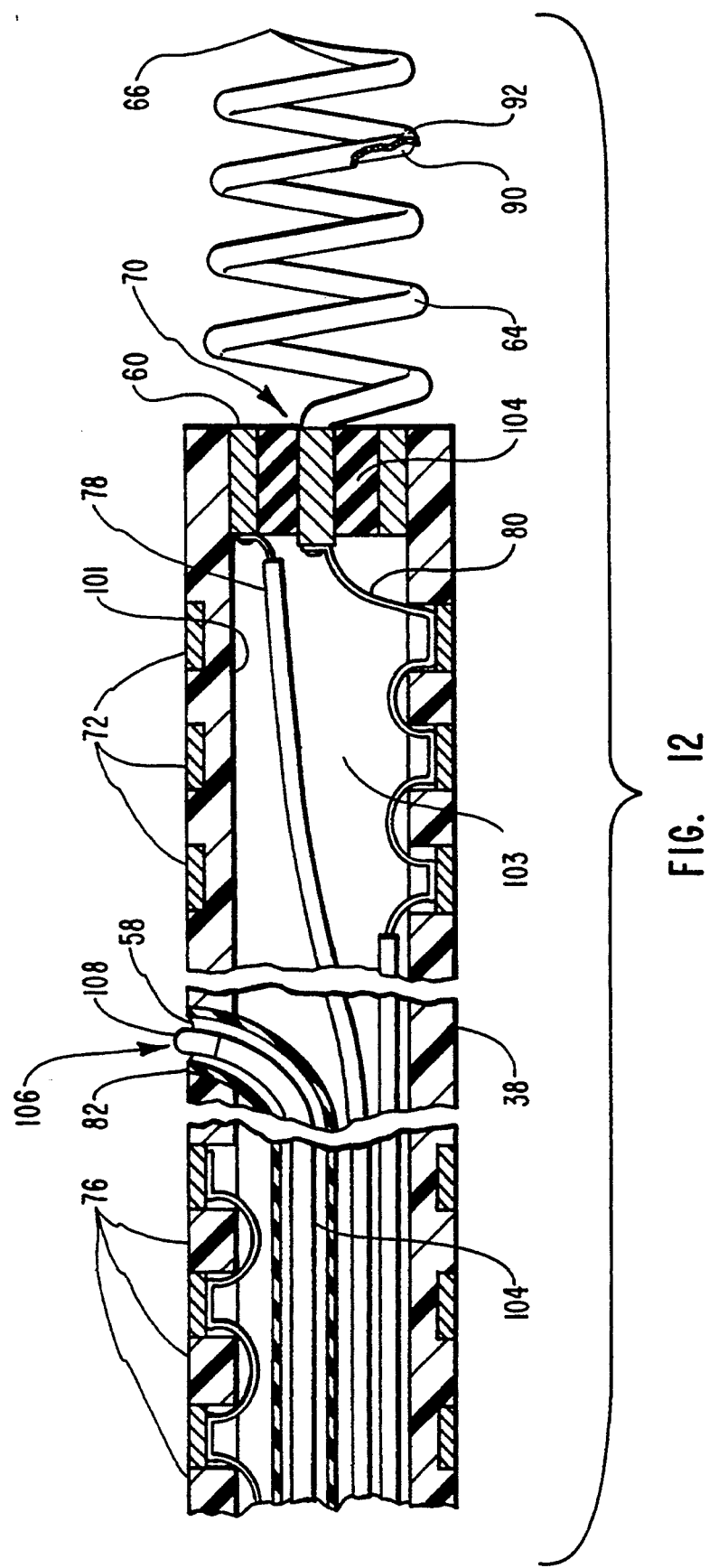
FIG. 12 is a longitudinal view showing one embodiment of the catheter in FIG. 4 in which the helix is secured to the distal end of the probe.

Depicted in FIG. 12 is a longitudinal view of one embodiment of catheter 38. Catheter 38 is shown as having a lumen 101 longitudinally disposed within catheter 38 and defining a channel 103. Located within channel 103 is atrial lumen 82. Shown disposed within atrial lumen 82 is an atrial demand pacer lead 104 having a distal end 106. Attached to distal end 106 is an atrial demand pacer electrode 108. Atrial demand pacer electrode 108 has the same structural and electrical parameters as demand pacer electrode 60 but serves an independent function.

Demand pacer electrode 60 functions, predominantly, to pace right ventricle 22 of heart 14. However, there are times when it is beneficial to pace both right atrium 20 and right ventricle 22. To this end, exit port 58 is positioned on catheter 38 so as to reside in right atrium 20 when defibrillator electrode 62 is anchored into septum 30. Thereby, atrial demand pacer electrode 108 can be positioned in right atrium 20 for demand pacing right atrium 20 by simply being inserted in atrial lumen 82.

Catheter 38, depicted in FIG. 12, shows helix 64 securely attached to end face 70. An insulation plug 109 is shown inserted between defibrillator electrode 62 and demand pacer electrode 60 to prevent the electrodes from contacting and electrically shorting. To anchor helix 64 in this embodiment, helix 64 is positioned against septum 30 as previously discussed, and the entire catheter 38 is rotated, thereby rotating helix 64 for advancement into interior 36 of septum 30.

Figure 13:
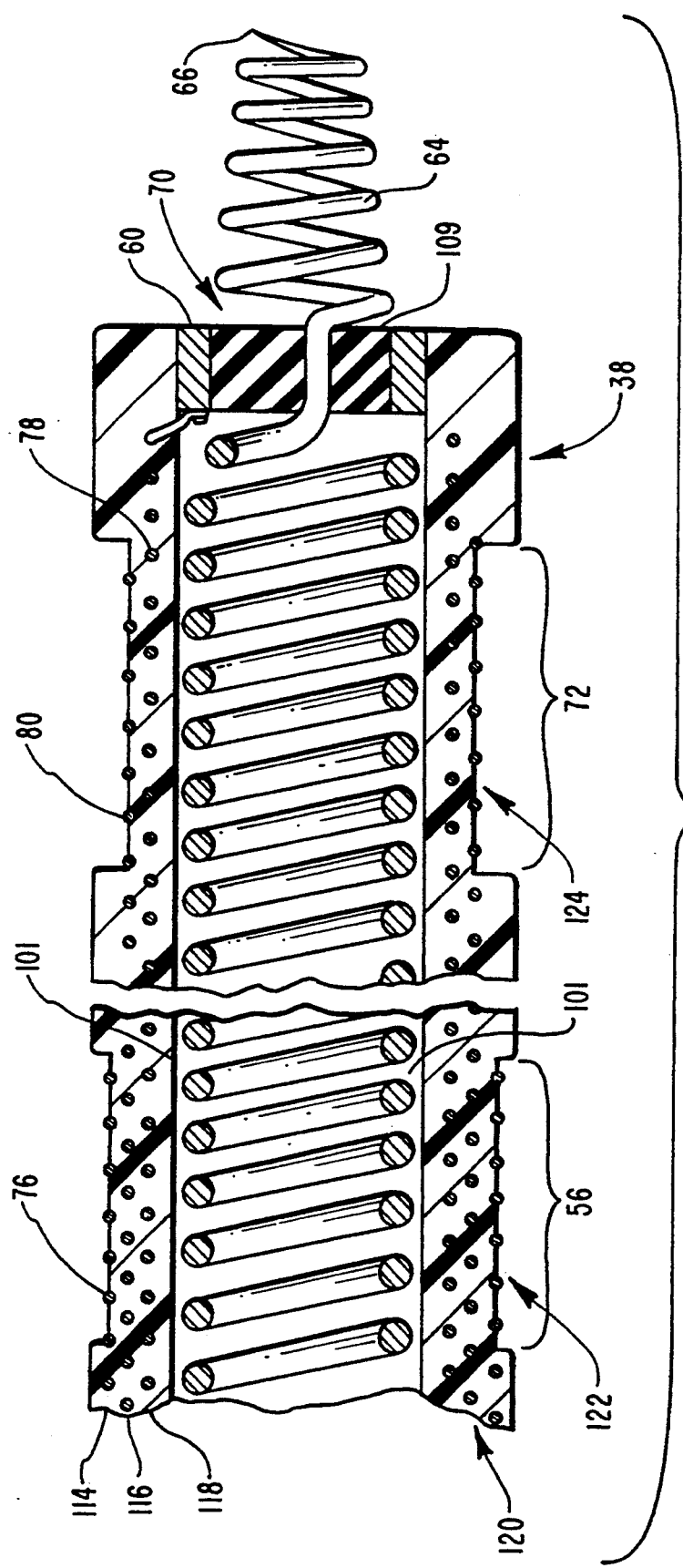
FIG. 13 is a longitudinal view of an alternative embodiment of the catheter in FIG. 4 in which the ground leads are partially exposed to form a ground electrode and the defibrillator leads are partially exposed to form a supplemental defibrillator electrode.

An additional alternative embodiment for catheter 38 is shown in a longitudinal view in FIG. 13. The figure reveals a first layer 114, a second layer 116, and a third layer 118 of lead wires 120 disposed in side wall 112 of catheter 38. Lead wires 120 are disposed in a spiral fashion so as to be disposed from proximal end 42 of probe 39 to distal end 40 of probe 39.

First layer 114 of lead wires 120 comprises ground lead 76. A first cutaway section 122 of probe 39 exposes a section of ground leads 76, thereby forming ground electrode 56. Second layer 116 of lead wires 120 comprises defibrillator lead 80. A second cutaway section 124 of probe 39 exposes defibrillator lead 80, thereby forming supplemental defibrillator electrode 72. Finally, third layer 118 of lead wires 120 comprises demand pacer lead 78 that is electrically coupled with demand pacer electrode 60.

By using lead wires 120 as the various electrodes, the traditional ring electrodes can be eliminated. Such an embodiment provides a more uniform flexibility to the probe. Furthermore, spirally disposing lead wires 120 within sidewall 112 of probe 39 adds structural support to probe 39, thereby increasing control of catheter 38 for inserting into heart 14. Additional support is provided to probe 39 in the embodiment in FIG. 13 by continuing helix 64 through interior 110 of probe 39. This embodiment of catheter 38 is also anchored to septum 30 by rotation of the entire catheter 38. However, there are alternative embodiments in which helix 64 is selectively and independently rotated of probe 39 for insertion into septum 30.

Figure 14:
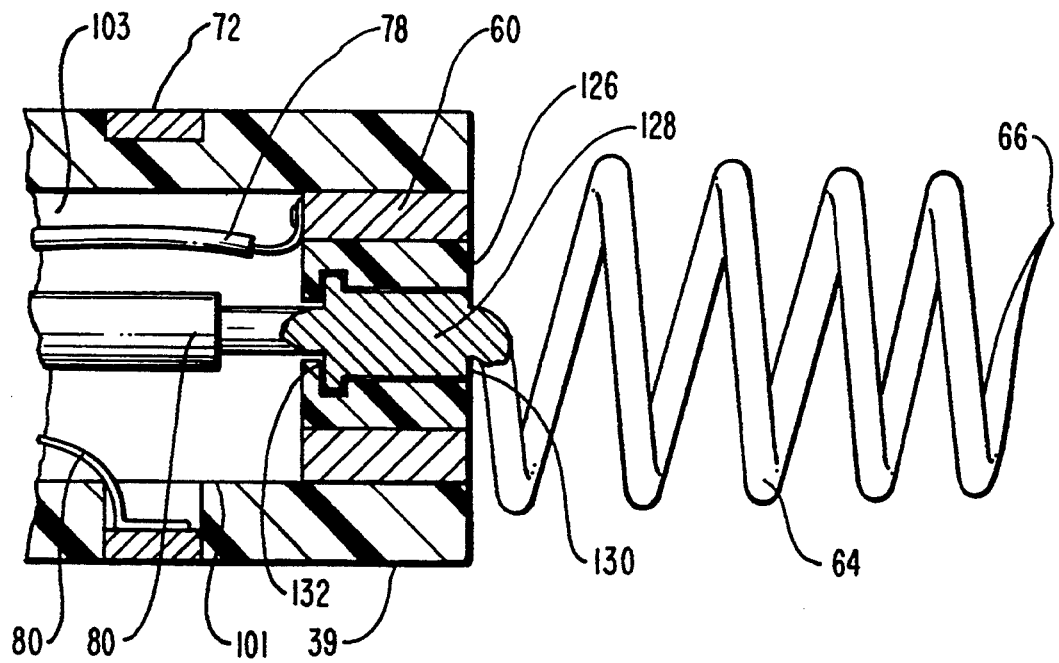
FIG. 14 is a longitudinal view of the tip of one embodiment of the catheter in FIG. 4 in which the defibrillator lead is disposed within the probe and is connected to the helical defibrillator electrode for selective and independent rotation of the helix.

In accordance with the present invention, there is also provided electrode installation means for selective independent rotation of helix 64 about the longitudinal access thereof to advance helix 64 into the interior 36 of septum 30. By way of example and not limitation, there is shown in FIG. 14 a sleeve 126 encasing a rotation plate 128 which is freely rotatable therein. Rotation plate 128 includes an exterior surface 130 from which defibrillator electrode 62 centrally projects therefrom and an interior surface 132 electrically coupled with and anchored to defibrillator lead 80. Thereby, independent rotation of defibrillator lead 80, rotates rotation plate 128 which in turn rotates helix 64 for insertion into interior 36 of septum 30.

Figure 15:
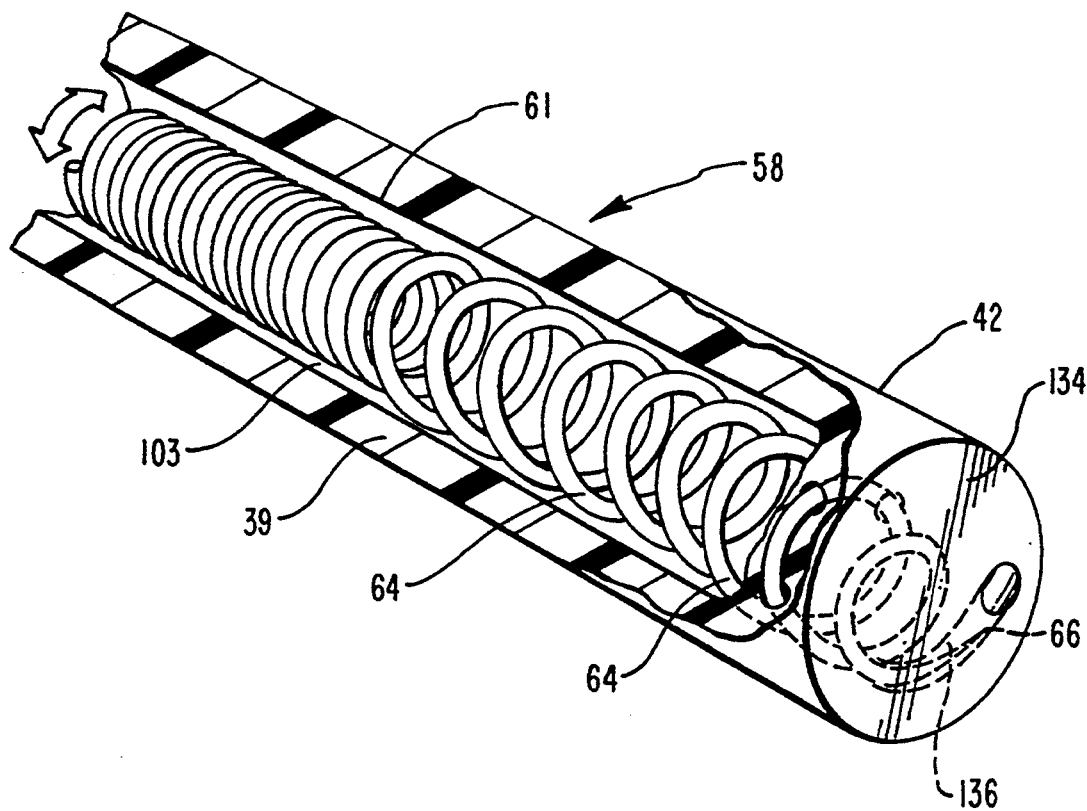
FIG. 15 is a longitudinal view of one embodiment of the tip of the catheter in FIG. 4 in which the helix is initially contained within the probe for easy insertion into the heart and can later be selectively rotated for insertion into the heart tissue.

An alternative embodiment for electrode installation means is depicted in FIG. 15. In this embodiment, helix 64 runs the length of probe 39 and is freely disposed therein. Positioned at tip 41 of probe 39 is a cap 134 having a bore 136 of a substantially complementary configuration of helix 64. Thereby, selective independent rotation of helix 64 permits the advancement of helix 64 through end cap 134 and into interior 36 of septum 30. The advantage of the embodiment shown in FIG. 15 is that helix 64 can remain in interior 110 while catheter 38 is being inserted into heart 14, thereby, inhibiting point 66 of helix 64 from damaging patient 10 as catheter 38 is being inserted.

Figure 16:
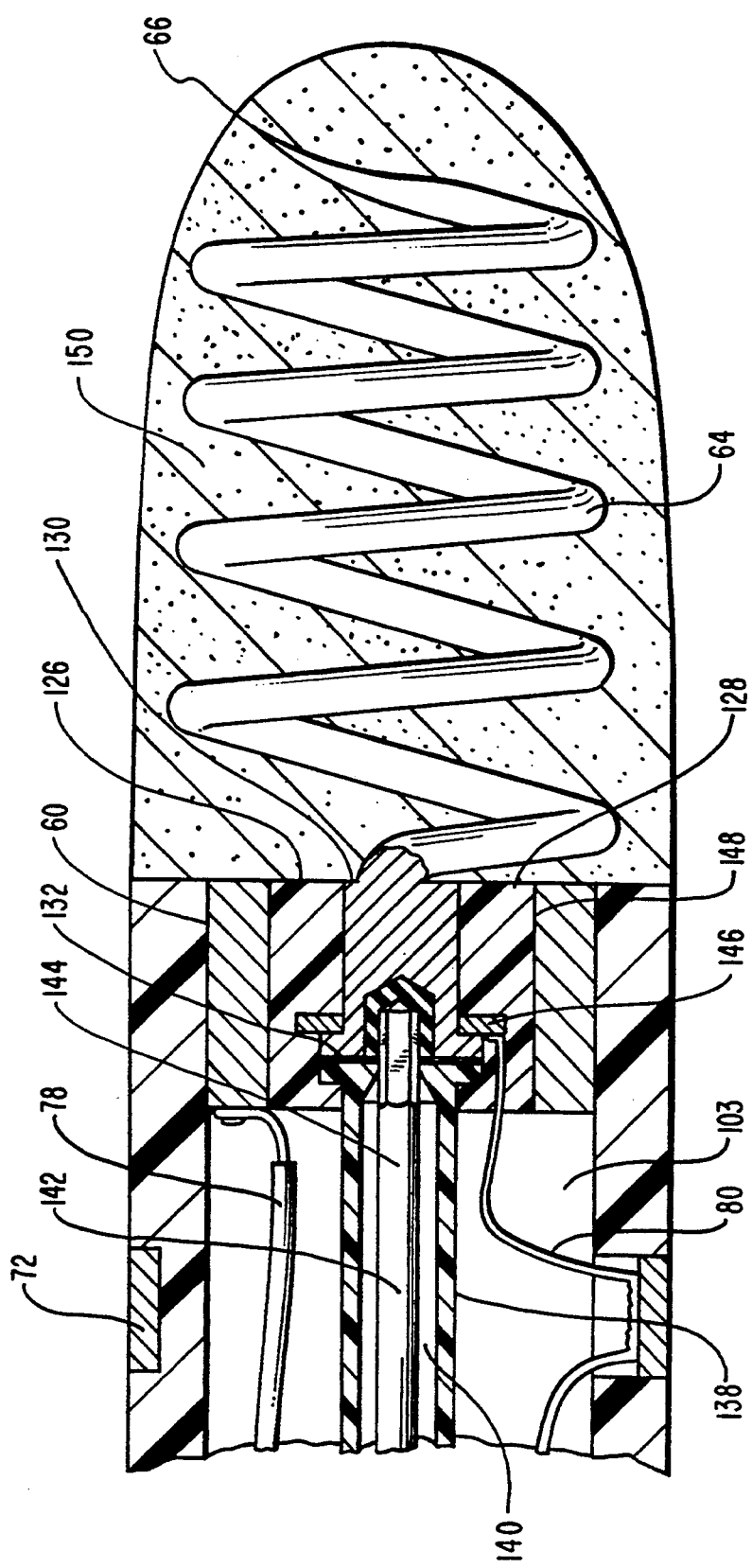
FIG. 16 is yet another longitudinal view of one embodiment of the tip of the catheter in FIG. 4 in which an inner lumen is disposed within the probe for receiving a stylet that can selectively and independently rotate the helical defibrillator electrode, the helix shown being encased in water soluble material for easy insertion into the heart.

Yet another embodiment for electrode installation means is depicted in FIG. 16. FIG. 16 reveals an inner lumen 138 longitudinally disposed within channel 103 of probe 39 from proximal end 42 to tip 41 of probe 39, inner lumen 138 having an inner channel 140. A steering stylet 142 having a first end 144 is freely disposed within inner channel 140 for selective rotation of helix 64. A benefit of inner lumen 138 is that steering stylet 142 can be positioned and rotated therein without the interference of any other leads which may be disposed in lumen 101.

In the embodiment shown in FIG. 16, rotation plate 128 is again disposed in sleeve 126 at tip 41 of probe 39 so as to freely rotate therein. Encircling rotation plate 128 is conductor sleeve 146. Conductor sleeve 146 is electrically coupled with defibrillator lead 80 and is structured to electrically communicate with rotation plate 128 for transferring a defibrillation pulse. Interior surface 132 of rotation plate 128 is exposed to inner channel 140 of inner lumen 138.

In accordance with the present invention there is also provided attaching means for coupling first end 144 of steering stylet 142 and interior surface 132 of rotation plate 128. By way of example and not limitation, there is shown in FIG. 16 interior surface 132 having a slot 148 capable of receiving first end 144 of steering stylet 142. First end 144 has a shape substantially complementary to slot 148. Thereby, independent rotation of steering stylet 142, rotates rotation plate 128 which in turn rotates helix 64 for insertion into septum 30.

Also depicted in FIG. 16 is a water soluble material 150 encasing defibrillator electrode 62. Water soluble material 150 acts to prevent point 66 of helix 64 from damaging patient 10 as catheter 38 is being inserted into heart 14. Once catheter 38 is inserted, water soluble material 150 dissolves, thereby permitting helix 64 to be inserted into septum 30 without obstruction. Water soluble material 150 can be made of materials such as sugar that can be melted into a liquid for attachment to helix 64 and can be dissolved in the blood without any detrimental effect to patient 10.

Figure 17:
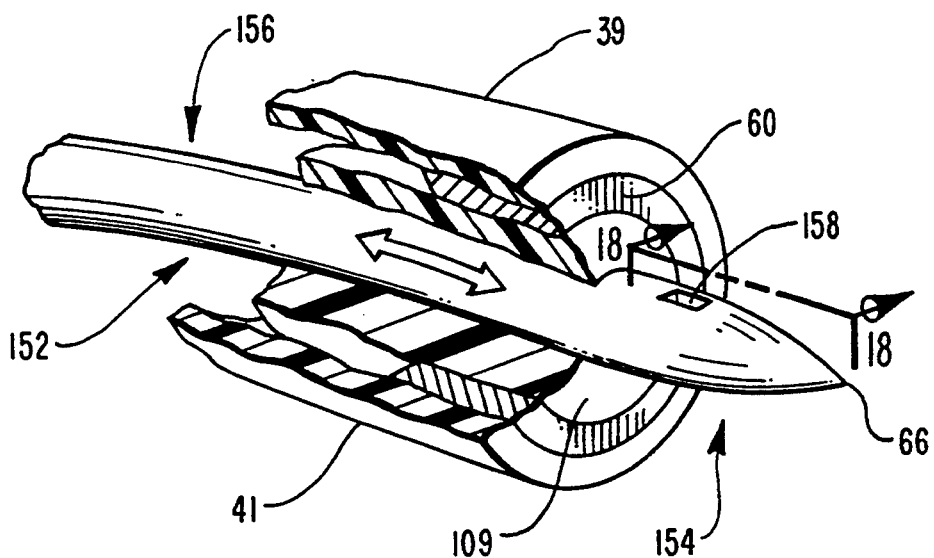
FIG. 17 is a cutaway side view of an embodiment of the catheter in FIG. 4, including the defibrillator electrode being a lance that is slidable within the probe.
Figure 18:
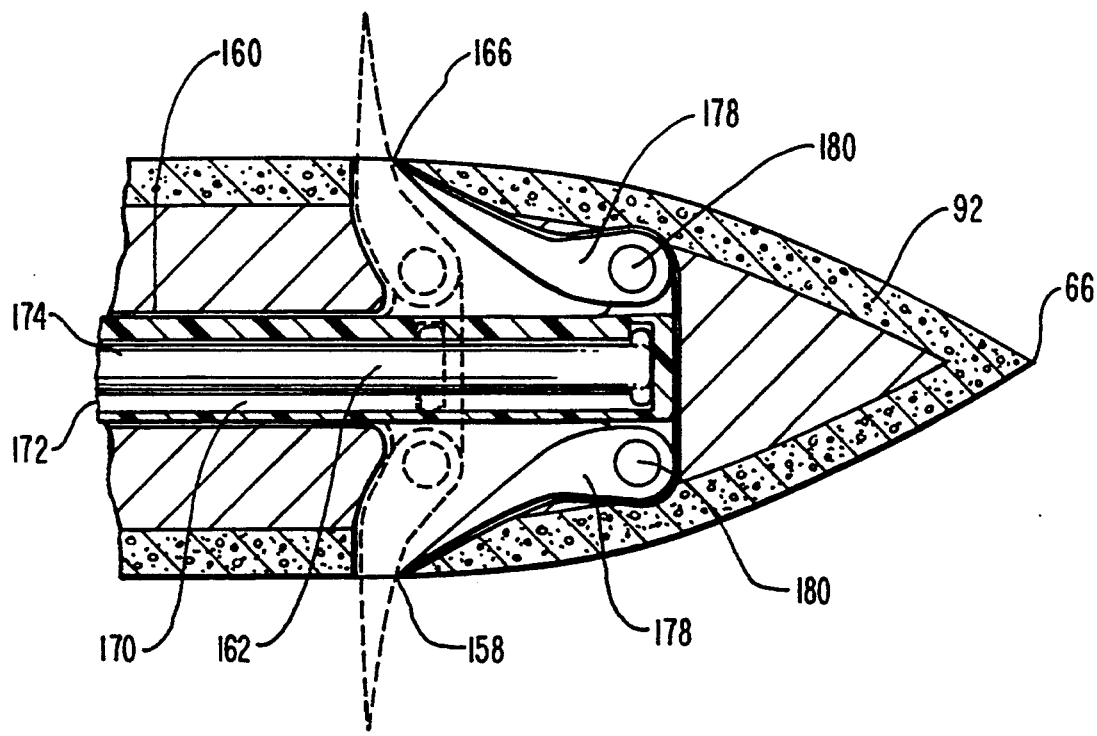
FIG. 18 is a longitudinal, enlarged view of the interior of the distal end of the lance in FIG. 17, including retractable barbs that can be expanded to secure the lance in the interior of the septum.

An alternative embodiment for the defibrillator means is shown in FIG. 17. By way of example and not limitation, there is shown in FIG. 17 a lance 152 having a distal end 154 and a side 156. Position on side 156 are exit ports 158. Lance 152 is shown as being freely disposed in probe 39. Depicted in FIG. 18 is an enlarged longitudinal view of distal end 154 of lance 152. Lance 152 is shown as comprising a duct 160 longitudinally disposed within lance 152. A retracting slot 164 is formed in distal end 154 of lance 152 so as to communicate with duct 160. Furthermore, communicating with retracting slot 164 are exit ports 158.

Disposed within duct 160 is a slidable shaft 170 having a first end 172 with a slot 174 capable of receiving and locking first end 163 of the steering stylet 162. Slidable shaft 170 has a second end 176 attached to barbs 178 by hinges 180. Slidable shaft 170 is structured to selectively project barbs 178 through exit ports 158 and to selectively retract barbs 178 into retraction slot 164 by withdrawing and advancing, respectively, slidable shaft 170. Accordingly, once distal end 154 of lance 152 is inserted into interior 36 of septum 30, barbs 178 can be projected for locking lance 152 into septum 30. To withdraw lance 152, barbs 178 are retracted into lance 152.

Figure 19:
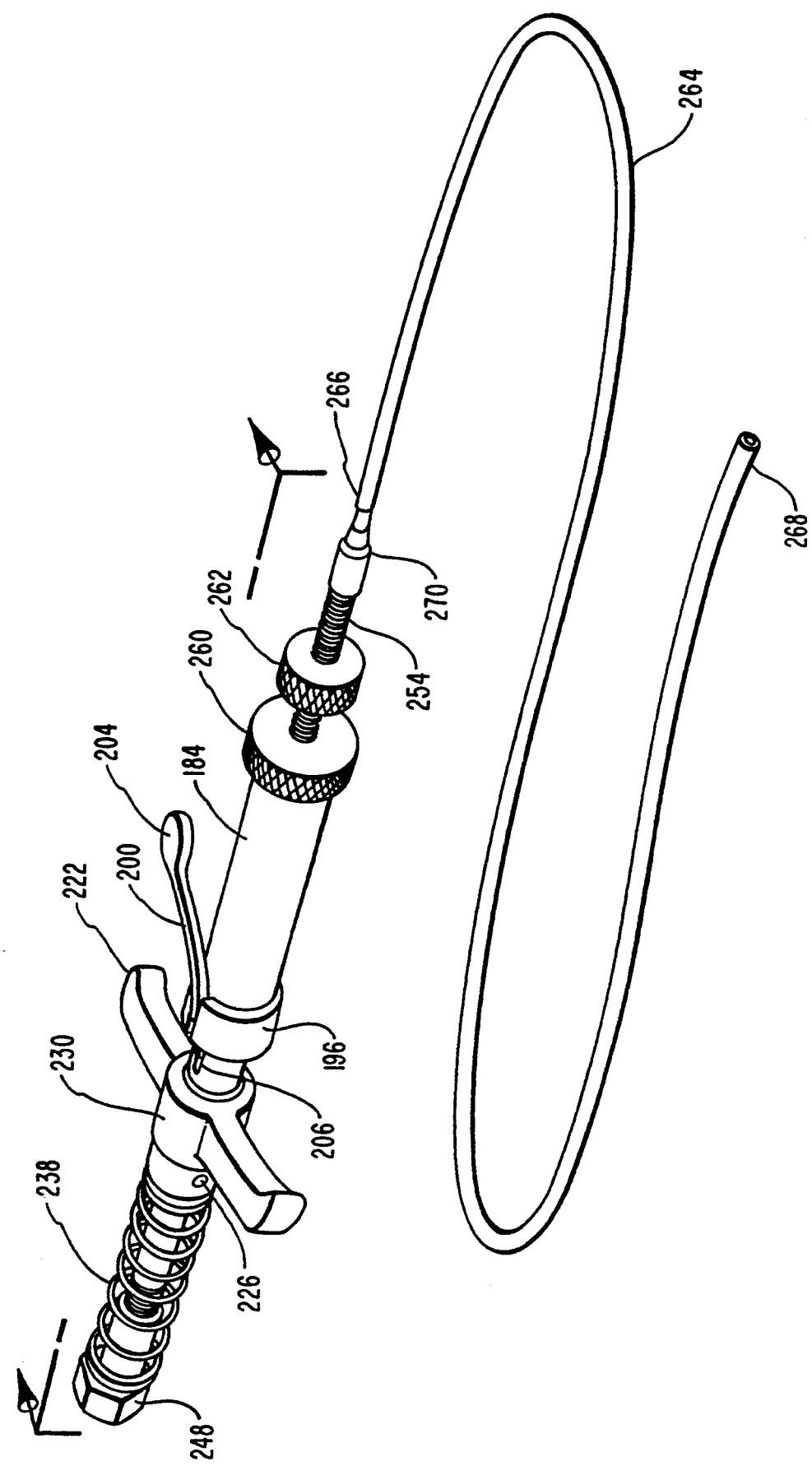
FIG. 19 is a perspective view of a spring gun used to propel the lance shown in FIG. 17 a predetermined distance into the interior of the septum.
Figure 20:
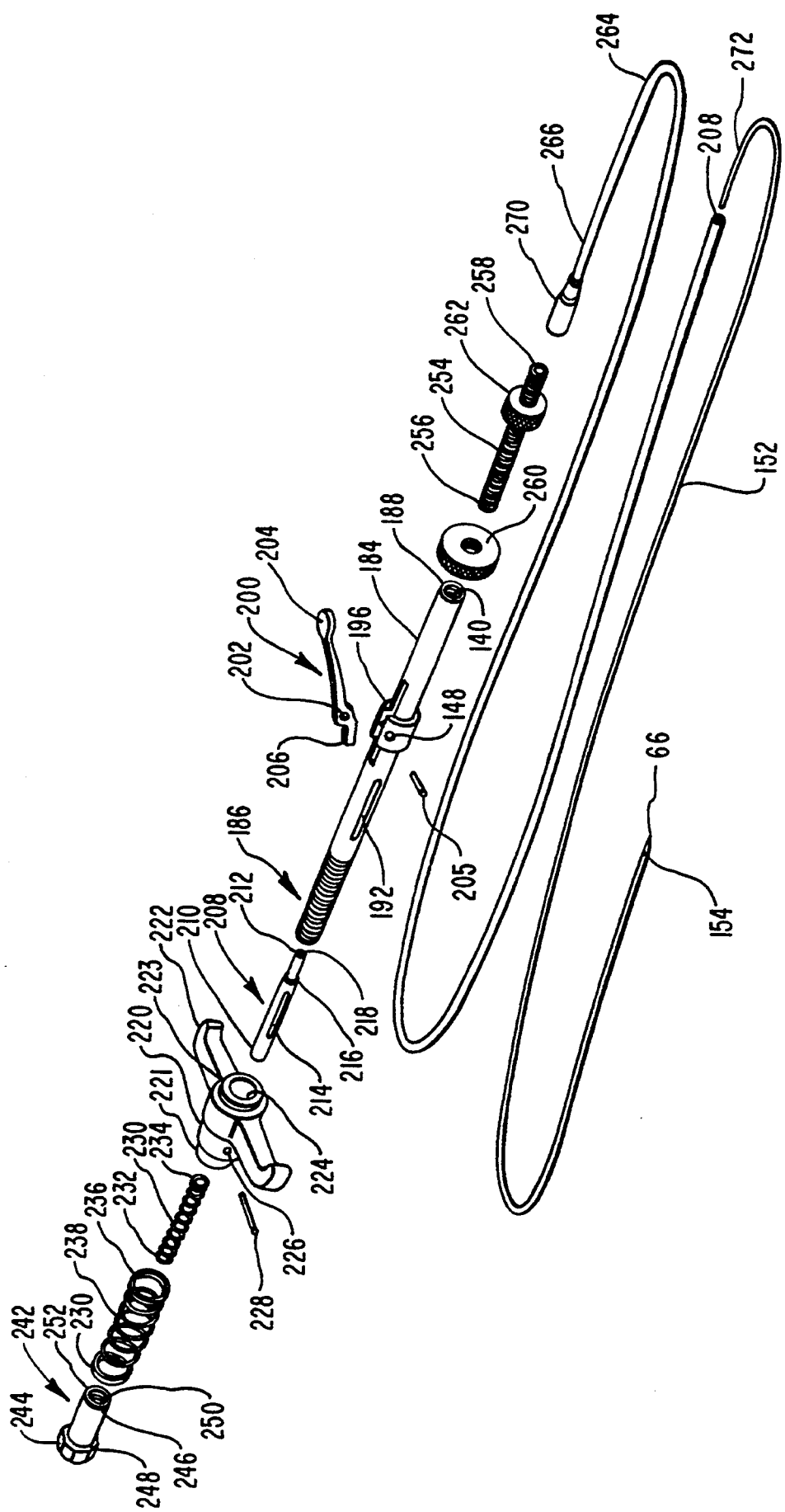
FIG. 20 is an exploded view of the spring gun shown in FIG. 19.
Figure 21:
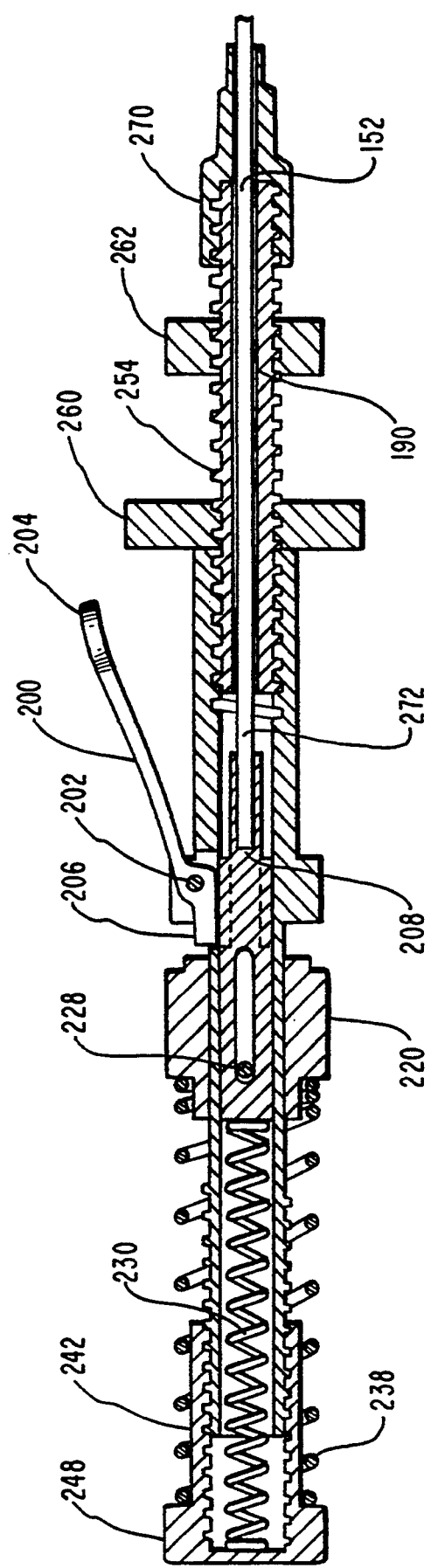
FIG. 21 is a longitudinal view of the spring gun shown in FIG. 19.

In accordance with the present invention there is also provided a propelling means for selectively applying a force to lance 152 to imbed lance 152 at a predetermined distance into interior 36 of septum 30. By way of example and not limitation, there is shown in FIGS. 19, 20, and 21 a spring gun 182. FIGS. 19–21 provide different views to spring gun 182: FIG. 19 is a perspective view, FIG. 20 is an exploded view and FIG. 21 is a longitudinal view.

Spring gun 182 comprises a body 184 having a first end 186, a second end 188, an inner channel 190, a side slot 192, a top slot 194, a clamp 196 attached about body 184 adjacent to top slot 194, and a hole 198 extending through clamp 196. Structured on first end 186 of body 184 are exterior threads 197 and structured at second end 188 in inner channel 190 are inner threads 199. Positioned in top slot 194 is latch 200 having a passage 202, a lever 204, and a key 206. Latch 200 is inserted in top slot 194 and rotatably attached to clamp 196 by inserting pin 205 through hole 198 and passage 202. Inserted in inner channel 190 is hammer pin 208 having a first end 210, a second end 212, a side opening 214, a notch surface 216, and an aperture 218 at second end 212. Hammer pin 208 is positioned in body 184 such that side opening 214 of hammer pin 208 and side slot 192 of body 184 are aligned.

Positioned onto body 184 is handle 220 having arms 222, longitudinal passage 224, bore 226, and locking pin 228. Handle 220 is positioned such that body 184 resides in longitudinal passage 224 with bore 226 being aligned with side slot 192 of body 184 and side opening 214 of hammer pin 208. Handle 220 and hammer pin 208 are slidably connected to body 184 by pin 228 residing in bore 226, side slot 192, and side opening 214.

Positioned against first end 210 of hammer pin 208 and within inner channel 190 of body 184 is pin spring 230. Pin spring 230 has a first end 232 and a second end 234. Positioned against first end 221 of handle 220 is second end 236 of handle spring 238. Handle spring 238 also has a first end 240. Attached to first end 186 of body 184 is adjusting knob 242 having a first end 244, a second end 246, a bevel 248, and an interior slot 250 having threads 252 therein. Adjusting knob 242 is positioned such that first end 240 of handle spring 238 resides against bevel 248 of adjusting knob 242 while first end 232 of pin spring 230 resides in interior slot 250 of adjusting knob 242.

Attached to second end 188 of body 184 is a screw bar 254. Screw bar 254 has a first end 256 and a second end 258. Screw bar 254 is attached to body 184 by screwing first end 256 of screw bar 254 into inner channel 190 of body 184. Positioned on screw bar 254 is first adjustment knob 260 and second adjustment knob 262. Finally, spring gun 182 is also depicted as having a sheath 264 with a first end 266, a second end 268, and a screw cap 270 positioned at first end 266. Sheath 264 is attached to screw bar 254 by screwing screw cap 270 of sheath 264 onto second end 258 of screw bar 254.

FIG. 20 also shows lance 152 having a proximal end 272. To operate spring gun 182 for inserting distal end 154 of lance 152 into septum 30, proximal end 272 of lance 152 is threaded through sheath 264, screw bar 254, and body 184 where proximal end 272 of lance 152 is inserted and attached to aperture 218 of hammer pin 208. Handle 220 is then pulled back towards adjusting knob 242, thereby also pulling back hammer pin 208 and compressing pin spring 230 and handle spring 238. Handle 220 is pulled back until notch surface 216 of hammer pin 208 is parallel with key 206 of latch 200 at which point lever 204 is lifted causing key 206 of lever 204 to catch against notch surface 216 of hammer pin 208. Handle 220 can now be pressed towards latch 200 such that second end 223 of handle 220 covers key 206 of latch 200, thereby forming a safety in which lever 204 cannot be depressed. To propel said lance, handle 220 is retracted to uncover key 206 of latch 200. Lever 204 is then depressed raising key 206 and allowing hammer pin 208 to be propelled under the pressure of pin spring 230, in turn, propelling lance 152 forward.

The distance that distal end 154 of lance 152 is projected from second end 268 of sheath 264 is regulated by screw bar 254. The farther, screw bar 254 is inserted into second end 188 of body 184, the more lance 152 projects from second end 268 of sheath 264 and; accordingly, the farther lance 152 will be inserted into interior 36 of septum 30. The force at which lance 152 is propelled from sheath 264 is regulated by adjustment knob 242. The farther adjustment knob 242 is screwed onto first end 186 of body 184, the more pin spring 230 is compressed, thereby increasing the projecting force.

Once lance 152 is inserted into septum 30, spring gun 182 can be removed from around lance 152. After which, probe 39 can be slid over proximal end 272 of lance 152 and pressed down to distal end 154 of lance 152, thereby producing an embodiment as shown in FIG. 17.

The method for inserting the catheter, as previously discussed, into the heart of a patient comprises the steps of:

1. making an incision into a blood vessel leading to the heart of the patient;
2. inserting the tip of the probe into the blood vessel through the incision;
3. threading the catheter through the blood vessel of the patient to the heart thereof and then through an atrium and into a ventricle of the heart so as to be positioned against the side wall of the muscular section of the septum; and
4. anchoring at least a portion of the defibrillator electrode directly to the interior of the septum of the heart.

In an alternative embodiment, the catheter can be inserted into the blood vessel and threaded to the heart through an introducer which is inserted into the blood vessel. Such introducers are well known in the art. Once the defibrillator electrode is anchored, the introducer can be removed. Anchoring the defibrillator electrode can be accomplished by rotating the entire probe so as to rotate the helix, thereby advancing the helix into the septum; or the helix can be rotated independent of the probe for selective insertion into the septum. Finally, the lance can be inserted into the septum either by simply pressing the lance into the septum or by use of the spring gun.

When the regulator is attached to the proximal end of the probe, the method can include the additional steps of sensing the pulse of the heart through electrically conductive pathway, analyzing in the controller the pulse of the heart obtained in the step of sensing, and transmitting electrical signals from the regulator to the electrically conductive pathway. The alternative electrical signals comprise the electrical defibrillation pulse and the electrical demand pacer pulse.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States patent is:

1. A method for inserting a catheter into the heart of a patient, the catheter comprising an elongated, flexible, electrically non-conductive probe having a proximal end and a distal portion terminating into a tip, the heart having a right atrium communicating with a right ventricle and a left atrium communicating with a left ventricle, the left ventricle being separated from the right ventricle by a septum, the septum having an outer wall in each of the left and right ventricles, the portion of the septum between the outer walls defining the interior of the septum, the septum also having a membranous section and a muscular section, the interior of the septum housing the bundle of His in the membranous section, said method comprising:
   (a) making an incision into a blood vessel leading to the heart of the patient;
   (b) inserting the tip of the probe into said blood vessel through said incision, the catheter further comprising a defibrillator electrode projecting from said tip;
   (c) threading the catheter through the blood vessel of the patient to the heart thereof and then through an atrium and into a ventricle of the heart so as to position said defibrillator electrode against the outer wall of the septum; and
   (d) anchoring said defibrillator electrode directly into the interior of the septum of the heart.

2. A method as recited in claim 1, wherein the blood vessel is a vein such that the probe is inserted into the right atrium of the heart.

3. A method as recited in claim 1, wherein the step of anchoring further comprises the step of inserting said defibrillator electrode into the interior of the septum so that the tip of the probe is in contact with an outer wall of the septum.

4. A method as recited in claim 1, wherein the step of anchoring includes the defibrillator electrode being anchored into the septum at a minimum distance of 5 cm from the bundle of His.

5. A method as recited in claim 1, wherein said portion of said defibrillator electrode anchored directly to the interior of the septum has an electrical surface area in a range between about 1.2 cm$^2$ and about 2.0 cm$^2$.

6. A method as recited in claim 1, wherein the step of anchoring includes the defibrillator electrode being anchored into the muscular section of the septum.

7. A method as recited in claim 1, wherein said defibrillator electrode comprises a helix having a longitudinal axis.

8. A method as recited in claim 7, wherein the step of anchoring includes selectively rotating said helix about said longitudinal axis independent of said probe to advance said helix into the interior of the septum.

9. A method as recited in claim 7, wherein the step of anchoring comprises rotating said probe attached to said helix, thereby to advance said helix into the interior of the septum.

10. A method for regulating the pulse of the heart of a patient through the use of a regulator and an implantable catheter, the regulator being electrically coupled with an electrically conductive pathway longitudinally disposed within the catheter, the catheter including an elongated, flexible, electrically non-conductive probe having a proximal end and a distal portion terminating in a tip, the heart having a right atrium communicating with a right ventricle and a left atrium communicating with a left ventricle, the left ventricle is separated from the right ventricle by a septum, the septum having an outer wall in each of the left and right ventricles, the portion of the septum between the outer walls defining the interior of the septum, the septum also having a membranous section and a muscular section, the interior of the septum housing the bundle of His in the membranous section, the method comprising the steps of:

(a) making an incision into a blood vessel in a path leading to the heart of the patient;

(b) inserting the tip of the probe into said blood vessel through said incision, said tip comprising:
  (i) an end face perpendicular to the probe;
  (ii) a helical defibrillator electrode electrically coupled with the electrically conductive pathway and centrally projecting from said end face; and
  (iii) a demand pacer electrode electrically coupled with the electrically conductive pathway and positioned on said end face at a distance from said helical defibrillator electrode;

(c) threading the catheter through the blood vessel of the patient to the heart thereof and then through an atrium and into a ventricle so as to position said helical defibrillator electrode against the outer wall, of the muscular section of the septum;

(d) rotating said helical defibrillator electrode so as to advance said helical defibrillator electrode directly into the muscular section of the interior of the septum of the heart so as to contact said demand pacer electrode to the outer wall of the septum;

(e) sensing the pulse of the heart through the electrically conductive pathway in the probe;

(f) analyzing in the regulator the pulse of the heart obtained in said step of sensing; and (g) transmitting alternative electrical signals from the regulator to the electrically conductive pathway depending on the results of said step of analyzing, said alternative electrical signals comprising:
  (i) an electrical defibrillation pulse transmitted to the helical defibrillator electrode when the heart needs to be defibrillated; and
  (ii) an electrical demand pacer pulse transmitted to the demand pacer electrode when the heart needs to be paced.

11. A method as recited in claim 10, wherein the blood vessel is a vein such that the probe is inserted into the right atrium of the heart.

12. A method as recited in claim 10, wherein said helical defibrillator electrode has an electrical surface area in a range between about 1.2 $cm^2$ and about 2.0 $cm^2$.

13. A method as recited in claim 10, wherein said helical defibrillator electrode has a porous electrical surface area.

14. A method as recited in claim 10, wherein the step of screwing includes selectively rotating said helical defibrillator electrode independent of said probe.

15. A method as recited in claim 10, wherein the step of screwing comprises rotating said probe attached to said helix, thereby advancing said helix into the interior of the septum.

16. A method for inserting a catheter into the heart of a patient, the catheter comprising an elongated, flexible, electrically non-conductive probe having a proximal end and a distal portion terminating into a tip, the heart having a right atrium communicating with a right ventricle and a left atrium communicating with a left ventricle, the left ventricle being separated from the right ventricle by a septum, the septum having an outer wall in each of the left and right ventricles, the portion of the septum between the outer walls defining the interior of the septum, the septum also having a membranous section and a muscular section, the interior of the septum housing the bundle of His in the membranous section, said method comprising:

(a) making an incision into a vein leading to the right atrium of the heart of the patient;

(b) inserting the tip of the probe into said vein through said incision, the catheter further comprising a defibrillator electrode projecting from said tip;

(c) threading the catheter through said vein of the patient to the heart thereof and then through the right atrium and into the right ventricle of the heart so as to position said defibrillator electrode against the outer wall of the muscular section of the septum; and (d) anchoring said defibrillator electrode directly into the interior of the muscular section of the septum of the heart.

* * * * *

UNITED STATES PATENT AND TRADEMARK OFFICE
CERTIFICATE OF CORRECTION

PATENT NO. : 5,374,287
DATED : December 20, 1994
INVENTOR(S) : LEO RUBIN

It is certified that error appears in the above-indentified patent and that said Letters Patent is hereby corrected as shown below:

Column 4, line 34, delete second occurrence of "is"
Column 5, line 2, "comprising" should be --comprises--
Column 10, line 54, after "tissue" insert --that--

Signed and Sealed this

Eighteenth Day of July, 1995

Attest:

BRUCE LEHMAN

Attesting Officer

Commissioner of Patents and Trademarks